United States Patent
Johnson et al.

(10) Patent No.: US 12,031,152 B2
(45) Date of Patent: Jul. 9, 2024

(54) NUTRIENT MEDIA FOR THE PRODUCTION OF SLAUGHTER-FREE MEAT

(71) Applicant: Upside Foods, Inc., Berkeley, CA (US)

(72) Inventors: Kalle Lukyan Johnson, Orinda, CA (US); Patricia R. Benton, Huntington Beach, CA (US); Cameron Gentry Copeland, Walnut Creek, CA (US); Sukhdeep Singh Dhadwar, El Cerrito, CA (US); Meri Teresa Firpo, Oakland, CA (US); Marie Elizabeth Gibbons, Emeryville, CA (US); Stephen K. Hsu, Albany, CA (US); Robert Sierra, Berkeley, CA (US); Kevin John Kayser, Chesterfield, MO (US)

(73) Assignee: UPSIDE FOODS, INC., Berkeley, CA (US)

( * ) Notice: Subject to any disclaimer, the term of this patent is extended or adjusted under 35 U.S.C. 154(b) by 0 days.

(21) Appl. No.: 17/341,220

(22) Filed: Jun. 7, 2021

(65) Prior Publication Data
US 2022/0073870 A1 Mar. 10, 2022

Related U.S. Application Data

(60) Provisional application No. 63/035,661, filed on Jun. 5, 2020.

(51) Int. Cl.
*C12N 5/071* (2010.01)

(52) U.S. Cl.
CPC ........ *C12N 5/0602* (2013.01); *C12N 2500/14* (2013.01); *C12N 2500/24* (2013.01); *C12N 2500/32* (2013.01); *C12N 2500/34* (2013.01); *C12N 2500/36* (2013.01); *C12N 2500/38* (2013.01); *C12N 2501/105* (2013.01); *C12N 2501/11* (2013.01); *C12N 2501/113* (2013.01); *C12N 2501/115* (2013.01); *C12N 2501/117* (2013.01); *C12N 2501/12* (2013.01); *C12N 2501/135* (2013.01); *C12N 2501/15* (2013.01); *C12N 2501/155* (2013.01); *C12N 2501/165* (2013.01); *C12N 2501/33* (2013.01)

(58) Field of Classification Search
CPC .................................................. C12N 5/0602
See application file for complete search history.

(56) References Cited

PUBLICATIONS

Russo et al., 2019, Pharmaceuticals, vol. 11, pp. 1-17 (Year: 2019).*
FDA List of CFR Title 21, three page web printout (Year: 2022).*
ECHEMI.com printout for sodium molybdate, three pages (Year: 2022).*
2009, IPCS, Environmental Health Criteria 240, Chapter 5 (Year: 2009).*
Five American Food Ingredients That Are Banned in Other Countries, 10 page web printout (Year: 2022).*
Final Determination Regarding Partially Hydrogenated Oils—FDA Ruling (Year: 2013).*
FDA Notice for Synthetic Flavorings (Year: 2018).*
Rouiller et al. (2013, mAbs, vol. 5:3, pp. 501-511).*
Allan, S.J. et al., "Bioprocess Design Considerations for Cultured Meat Production With a Focus on the Expansion Bioreactor," Frontiers in Sustainable Food Systems, vol. 3, Jun. 12, 2019, pp. 1-9.
Andreassen, R.C. et al., "Screening of by-products from the food industry as growth promoting agents in serum-free media for skeletal muscle cell culture," Food & Function, vol. 11, Iss. 3, Mar. 2, 2020, pp. 2477-2488.
Anonymous, "EPOP:GNO83316," Mar. 2, 2009, one page, [Online] [Retrieved on Sep. 9, 2021] Retrieved from the Internet <URL: https://ibis.internal.epo.org/exam/dbfetch.jsp?id=EPOP:GNO83316>.
Anonymous, "GSP:AFS76940," Jun. 14, 2007, one page, [Online] [Retrieved on Sep. 9, 2021] Retrieved from the Internet <URL: https://ibis.internal.epo.org/exam/dbfetch.jsp?id=GSP:AFS76940>.
Anonymous, "GSP:BDB47673," Aug. 11, 2016, one page, [Online] [Retrieved on Sep. 9, 2021] Retrieved from the Internet <URL: https://ibis.internal.epo.org/exam/dbfetch.jsp?id=GSP:BDB47673>.
Anonymous, "GSP:BDC70983," Jul. 21, 2016, one page, [Online] [Retrieved on Sep. 9, 2021] Retrieved from the Internet <URL: https://ibis.internal.epo.org/exam/dbfetch.jsp?id=GSP:BDC70983>.
Anonymous, "UPI0003C87471," Jan. 6, 2015, one page, [Online] [Retrieved on Sep. 9, 2021] Retrieved from the Internet <URL: https://www.uniprot.org/uniparc/UPI0003C87471 >.
Bhat, Z.F. et al., "Animal-free Meat Biofabrication," American Journal of Food Technology 6(6), May 15, 2011, pp. 441-459.
PCT International Search Report and Written Opinion, PCT Application No. PCT/US2021/036264, dated Sep. 24, 2021, 16 pages.
Thermo Fisher Scientific, "11965—DMEM, high glucose," Jul. 4, 1959, pp. 1-2, [Online] [Retrieved on Sep. 9, 2021] Retrieved from the Internet <URL: https://www.thermofisher.com/de/de/home/technical-resources/media-formulation.8.html>.

* cited by examiner

*Primary Examiner* — Anoop K Singh
*Assistant Examiner* — David A Montanari
(74) *Attorney, Agent, or Firm* — Ballard Spahr LLP

(57) ABSTRACT

Provided herein are nutrient media formulations and engineered growth factors, and methods thereof, useful for the production of slaughter-free meat.

19 Claims, 6 Drawing Sheets
Specification includes a Sequence Listing.

SEQUENCE LISTING

```
<160> NUMBER OF SEQ ID NOS: 7

<210> SEQ ID NO 1
<211> LENGTH: 83
<212> TYPE: PRT
<213> ORGANISM: Gallus gallus

<400> SEQUENCE: 1

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
            20                  25                  30

Asp Arg Gly Phe Tyr Phe Ser Lys Pro Thr Gly Tyr Gly Ser Ser Ser
        35                  40                  45

Arg Arg Leu His His Lys Gly Ile Val Asp Glu Cys Cys Phe Gln Ser
    50                  55                  60

Cys Asp Leu Arg Arg Leu Glu Met Tyr Cys Ala Pro Ile Lys Pro Pro
65                  70                  75                  80

Lys Ser Ala

<210> SEQ ID NO 2
<211> LENGTH: 83
<212> TYPE: PRT
<213> ORGANISM: Homo sapiens

<400> SEQUENCE: 2

Met Phe Pro Ala Met Pro Leu Ser Ser Leu Phe Val Asn Gly Pro Arg
1               5                   10                  15

Thr Leu Cys Gly Ala Glu Leu Val Asp Ala Leu Gln Phe Val Cys Gly
```

```
                    20                  25                  30

Asp Arg Gly Phe Tyr Phe Asn Lys Pro Thr Gly Tyr Gly Ser Ser Ser
                35                  40                  45

Arg Arg Ala Pro Gln Thr Gly Ile Val Asp Glu Cys Cys Phe Arg Ser
        50                  55                  60

Cys Asp Leu Arg Arg Leu Glu Met Tyr Cys Ala Pro Leu Lys Pro Ala
65                  70                  75                  80

Lys Ser Ala

<210> SEQ ID NO 3
<211> LENGTH: 155
<212> TYPE: PRT
<213> ORGANISM: Artificial Sequence
<220> FEATURE:
<223> OTHER INFORMATION: universal FGF-2

<400> SEQUENCE: 3

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Ser Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 4
<211> LENGTH: 471
<212> TYPE: DNA
<213> ORGANISM: Artificial Sequence
<220> FEATURE:
<223> OTHER INFORMATION: universal FGF-2

<400> SEQUENCE: 4
atggcagcag gtagtattac tacgcttccc gcccttcccg aagacggggg ttcaggtgcc      60
ttcccgccgg gcattttaa agacccgaag cgccttact gtaagaatgg ggctttttc      120 ttgcgtatcc acccagacgg ccgcgtggac ggtgtgcgtg aaaaatccga tccacatatt    180
aaacttcagc ttcaagcaga agagcgtggt gtggtttcca tcaagggggt gtgtgccaac    240
cgctatcttg cgatgaagga ggacggtcgt ctgctggctt cgaaatgtgt taccgacgag    300
tgttttttct tcgagcgcct ggaatcaaat aattacaaca cctaccgcag ccgcaaatat    360
tcttcatggt acgtggcttt gaagcgcaca ggtcagtata aattgggcag taaaacgggt    420
ccaggacaga aggcgattct tttcttaccg atgtcagcta aaagctaatg a            471
```

<210> SEQ ID NO 5
<211> LENGTH: 108
<212> TYPE: PRT
<213> ORGANISM: Artificial Sequence
<220> FEATURE:
<223> OTHER INFORMATION: universal PDGF-BB

<400> SEQUENCE: 5

```
Ser Leu Gly Ser Leu Ala Ala Ala Glu Pro Ala Val Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Asp Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Val Ala Arg Ala Val Thr
            100                 105
```

<210> SEQ ID NO 6
<211> LENGTH: 153
<212> TYPE: PRT
<213> ORGANISM: Artificial Sequence
<220> FEATURE:
<223> OTHER INFORMATION: universal IGF-1

<400> SEQUENCE: 6

```
Met Gly Lys Ile Ser Ser Leu Pro Thr Gln Leu Phe Lys Cys Cys Phe
1               5                   10                  15

Cys Asp Phe Leu Lys Val Lys Met His Val Thr Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln His Thr Asp
        115                 120                 125

Met Pro Lys Ala Gln Lys Glu Val His Leu Lys Asn Thr Ser Arg Gly
    130                 135                 140

Ser Ala Gly Asn Lys Asn Tyr Arg Met
145                 150
```

<210> SEQ ID NO 7
<211> LENGTH: 190
<212> TYPE: PRT
<213> ORGANISM: Artificial Sequence
<220> FEATURE:
<223> OTHER INFORMATION: universal VEGF-A

```
<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gln Lys Pro His Glu Val Val Lys Phe Met Asp Val Tyr Gln Arg
            35                  40                  45

Ser Phe Cys Arg Pro Ile Glu Thr Leu Val Asp Ile Phe Gln Glu Tyr
    50                  55                  60

Pro Asp Glu Ile Glu Phe Ile Phe Lys Pro Ser Cys Val Pro Leu Met
65                  70                  75                  80

Arg Cys Gly Gly Cys Cys Asn Asp Glu Ser Leu Glu Cys Val Pro Thr
                85                  90                  95

Glu Glu Phe Asn Ile Thr Met Gln Ile Met Arg Ile Lys Pro His Gln
                100                 105                 110

Ser Gln His Ile Gly Glu Met Ser Phe Leu Gln His Asn Lys Cys Glu
            115                 120                 125

Cys Arg Pro Lys Lys Asp Lys Ala Arg Gln Glu Asn Pro Cys Gly Pro
    130                 135                 140

Cys Ser Glu Arg Arg Lys His Leu Phe Val Gln Asp Pro Gln Thr Cys
145                 150                 155                 160

Lys Cys Ser Cys Lys Asn Thr Asp Ser Arg Cys Lys Ala Arg Gln Leu
                165                 170                 175

Glu Leu Asn Glu Arg Thr Cys Arg Cys Asp Lys Pro Arg Arg
                180                 185                 190
```

NUTRIENT MEDIA FOR THE PRODUCTION OF SLAUGHTER-FREE MEAT

CROSS-REFERENCE TO RELATED APPLICATIONS

This application claims priority to U.S. provisional patent application No. 63/035,661, filed on Jun. 5, 2020, the contents of which are incorporated herein by reference in its entirety.

INCORPORATION BY REFERENCE OF SEQUENCE LISTING

This application contains a Sequence Listing which has been submitted in ASCII format via EFS-WEB and is hereby incorporated by reference in its entirety. Said ASCII copy, created on Jun. 4, 2021 is named MPHM_015_01US_SeqList_ST25.txt and is 7.97 kilobytes in size.

BACKGROUND

Adoption of meat produced by culturing metazoan cells in vitro as an alternative to traditional animal meat, obtained from slaughtered animals, is gaining momentum. Such meat (also referred to herein interchangeably as cell-based meat, in vitro produced cell-based meat, cell culture-based meat, in vitro meat, cultured meat, lab-grown meat, or clean meat) offers a sustainable alternative to traditional meat and overcomes associated drawbacks such as microbial contamination and exposure to hormones and antibiotics. It also provides several environmental benefits including conservation of land and water usage, high calorific conversion, and reduction of greenhouse gas emissions. Additionally, it addresses animal welfare concerns correlated with traditional meat production.

A barrier to the widespread adoption of cell-based meat is its relatively high cost. Production of cell-based meat is intricately linked to the cell culture media used in its cultivation and is currently estimated to account for about 80% of the cost of the end product. Formulation of cell culture media for cell-based meat production presents unique challenges, such as scalability, safety and regulatory considerations, and cost efficiency. Serum, derived from animal sources, like fetal bovine serum, is a common component of most cell culture media, providing an essential mixture of nutrients and proteins for efficient cell culture. However, animal-derived serum is currently not available at the industrial scale needed for the culture of cell-based meat. Use of animal-derived serum can also introduce batch-to-batch variability and dangerous pathogens due to its heterogeneous animal origin, and thus requires more involved quality control measures.

As cell-based meat comes closer to the marketplace, agencies such as the FDA and USDA, and their international counterparts, will be called upon to provide safety and regulatory oversight. The cell culture media used in cell-based meat cultivation, and its components, might be considered by the FDA as a food additive requiring regulatory oversight.

Hence, there is an unmet need for developing cell culture media formulations for the production of cell-based meat that satisfy high safety standards, cost efficiency, applicability at industrial scale, and that contains minimal or no animal-derived serum and/or other animal-derived components. Provided herein are novel cell culture media compositions and methods for the production of cell-based meat that address these and related needs.

SUMMARY

Provided herein are compositions and methods related to the production and use of nutrient media for production of slaughter-free meat.

Accordingly, in one aspect, provided herein, is an edible nutrient medium for the production of slaughter-free meat, the medium comprising a plurality of ingredients, wherein each ingredient is approved for use in food and/or is at or below its ADI value. In some embodiments the ingredient approved for use in food is Generally Recognized As Safe (GRAS). In some embodiments the ingredient is approved for use in food by the FDA, USDA, *Codex alimentarius*, European Food Safety Authority, and/or the Food Chemicals *Codex*.

In some embodiments the medium contains no more than 10%, 9%, 8%, 7%, 6%, 5%, 4%, 3%, 2%, 1%, 0.5%, 0.1%, 0.05% or no more than 0.01%% animal-derived serum. In some embodiments the medium is substantially free of animal-derived serum or free of animal-derived serum. In some embodiments the medium contains no more than 10%, 9%, 8%, 7%, 6%, 5%, 4%, 3%, 2%, 1%, 0.5%, 0.1%, 0.05% or no more than 0.01%% animal-derived components. In some embodiments the medium is substantially free of animal-derived components or free of animal-derived components. In some embodiments the medium is chemically defined.

In some embodiments the medium further comprises a growth factor. In some embodiments the medium further comprises a universal growth factor. In some embodiments the universal growth factor is FGF-2. In some embodiments the universal FGF-2 comprises an amino acid sequence set forth in SEQ ID NO: 3. In some embodiments the universal FGF-2 is encoded by a nucleic acid sequence set forth in SEQ ID NO: 4.

In some embodiments the universal growth factor is PDGF-BB. In some embodiments the universal PDGF-BB comprises an amino acid sequence set forth in SEQ ID NO: 5.

In some embodiments the universal growth factor is IGF-1. In some embodiments the universal IGF-1 comprises an amino acid sequence set forth in SEQ ID NO: 6.

In some embodiments the universal growth factor is VEGF-A. In some embodiments the universal VEGF-A comprises an amino acid sequence set forth in SEQ ID NO: 7.

In some embodiments the medium is used for culturing slaughter-free meat and the growth factor is a cis growth factor, wherein the cis growth factor matches the genus of the cells in culture. In some embodiments the use of the cis growth factor allows for enhanced cell growth or meat production compared to a non-cis growth factor. In some embodiments the cis growth factor that allows for enhanced cell growth compared to a non-cis growth factor is cis *Gallus* transferrin. In some embodiments the cis growth factor is a variant of the corresponding naturally existing growth factor of the genus of the cells in culture. In some embodiments the cis growth factor variant is *Gallus* LR3-IGF1. In some embodiments the *Gallus* LR3-IGF1 comprises an amino acid sequence set forth in SEQ ID NO: 1.

In some embodiments the growth factor is selected from the group consisting of IGF1, LR3-IGF1, FGF-1, FGF-2, PDGF, CTGF, EGF, TGFB, BMP, HGF, transferrin, insulin, WNT, interleukins, albumin, VEGF, homologs, paralogs, orthologs, variants, precursors, isoforms, and combinations thereof. In some embodiments the growth factor is optionally selected from Table 10. In some embodiments the growth factor is a chicken growth factor, duck growth factor, bovine growth factor, sheep growth factor, fish growth factor, porcine growth factor, mammalian growth factor, avian growth factor, reptile growth factor, amphibian growth factor, arachnid growth factor or teleost growth factor.

In some embodiments the medium comprises an adhesion protein. In some embodiments the adhesion protein is optionally selected from Table 14.

In some embodiments the plurality of ingredients comprises one or more amino acids, optionally at the concentration range provided in Table 1.

In some embodiments the plurality of ingredients comprises one or more carbohydrates, optionally at the concentration range provided in Table 2.

In some embodiments the plurality of ingredients comprises one or more vitamins, optionally at the concentration range provided in Table 3.

In some embodiments the plurality of ingredients comprises one or more inorganic salts, optionally at the concentration range provided in Table 4.

In some embodiments the plurality of ingredients comprises one or more trace metals, optionally at the concentration range provided in Table 5.

In some embodiments the plurality of ingredients comprises one or more lipids, optionally at the concentration range provided in Table 6.

In some embodiments the plurality of ingredients comprises one or more food oils, optionally at the concentration range provided in Table 6.

In some embodiments the plurality of ingredients comprises one or more growth factors, optionally at the concentration range provided in Table 12.

In some embodiments the plurality of ingredients comprises one or more supplementary ingredients, optionally at the concentration range provided in Table 8.

In some embodiments the plurality of ingredients comprises one or more TCA cycle intermediates, optionally at the concentration range provided in Table 7.

In some embodiments the plurality of ingredients comprises one or more glycolysis intermediates, iron carriers, ferric maltol, ferrous gluconate, shear protectants, polyethylene glycol, methylcellulose, and hydrolysates. In some embodiments the medium is admixed with water to form a solution.

In some embodiments the medium comprises methylcellulose. In some embodiments the medium comprises cyanocobalamin, optionally at a concentration range of 1.00E+05 g/L to 0.0026 g/L. In some embodiments the medium comprises simethicone. In some embodiments the medium comprises ferric ammonium citrate, optionally at a concentration range of 0.01 g/L to 0.5 g/L. In some embodiments the medium comprises food-grade plant oils.

In another aspect, provided herein, is a composition comprising any one or more of the media described above. In some embodiments the composition further comprises non-human cells in culture. In some embodiments the non-human cells are from poultry, seafood, game or livestock. In some embodiments the plurality of ingredients comprises one or more amino acids, magnesium salts, sodium salts, copper salts, zinc salts, iron salts, and vitamins, optionally at the concentration range provided in Table 9.

In another aspect, provided herein are engineered growth factors. In some embodiments, provided herein is a universal FGF-2 comprising the amino acid sequence set forth in SEQ ID NO: 3. In some embodiments provided herein is a universal FGF-2 encoded by the nucleic acid sequence set forth in SEQ ID NO: 4. In some embodiments provided herein is a universal PDGF-BB comprising the amino acid sequence set forth in SEQ ID NO: 5. In some embodiments provided herein is a universal IGF-1 comprising the amino acid sequence set forth in SEQ ID NO: 6. In some embodiments provided herein is a universal VEGF-A comprising the amino acid sequence as in SEQ ID NO: 7. In some embodiments provided herein is a *Gallus* LR3-IGF1 comprising the amino acid sequence set forth in SEQ ID NO: 1.

In another aspect, provided herein is a method for formulating a nutrient medium for the production of slaughter-free meat comprising: (a) providing a plurality of ingredients; and (b) one or more of: (i) replacing one or more ingredients currently not approved for use in food with an ingredient approved for use in food; (ii) removing one or more ingredients currently not approved for use in food; and (iii) formulating one or more ingredients currently not approved for use in food at or below ADI value. In some embodiments the medium contains no more than 10%, 9%, 8%, 7%, 6%, 5%, 4%, 3%, 2%, 1%, 0.5%, 0.1%, 0.05% or no more than 0.01%% animal-derived serum. In some embodiments the medium is substantially free of animal-derived serum or is free of animal-derived serum. In some embodiments the medium contains no more than 10%, 9%, 8%, 7%, 6%, 5%, 4%, 3%, 2%, 1%, 0.5%, 0.1%, 0.05% or no more than 0.01%% animal-derived components. In some embodiments the medium is substantially free of animal-derived components or free of animal-derived components. In some embodiments the medium is chemically defined.

In some embodiments of the method for formulating a nutrient medium for the production of slaughter-free meat, poloxamer is replaced with methylcellulose.

In some embodiments of the method for formulating a nutrient medium for the production of slaughter-free meat, cobalt chloride is replaced with cyanocobalamin.

In some embodiments of the method for formulating a nutrient medium for the production of slaughter-free meat, an anti-foaming agent currently not approved for use in food is replaced with simethicone.

In some embodiments of the method for formulating a nutrient medium for the production of slaughter-free meat, one or more of ammonium molybdate, sodium molybdate, ammonium metavanadate, sodium metavanadate, rubidium chloride and strontium chloride hexahydrate is replaced with ferric ammonium citrate.

In some embodiments the method for formulating a nutrient medium for the production of slaughter-free meat, further comprises adding any one or more of the growth factors described in the present disclosure. In some embodiments the method for formulating a nutrient medium for the production of slaughter-free meat, further comprises adding one or more of universal FGF-2, universal PDGF-BB, universal IGF-1, universal VEGF-A, and/or *Gallus* LR3-IGF1. In some embodiments the method for formulating a nutrient medium for the production of slaughter-free meat, further comprises adding one or more of SEQ ID NO. 1-7 or a sequence having at least about 50%, at least about 60%, at least about 70%, at least about 80%, at least about 90%, at least about 95%, at least about 96%, at least about 97%, at least about 98%, at least about 99% sequence identity thereto.

DETAILED DESCRIPTION

Figure 1A:
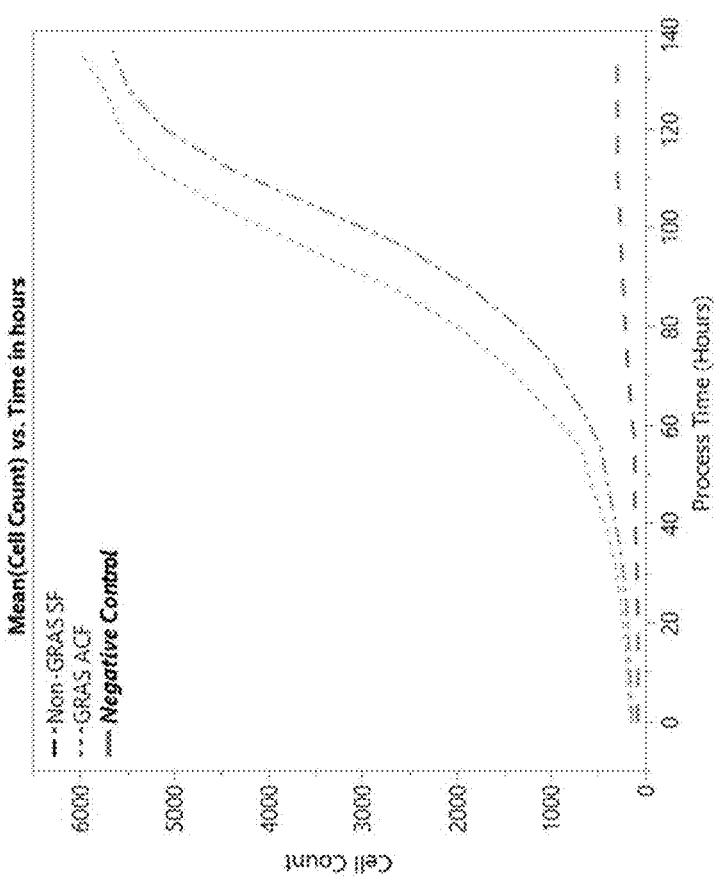
FIG. 1A shows a comparison of the growth of adherent *Gallus* cells cultured in a medium comprising Generally Recognized As Safe (GRAS) ingredients vs. growth in a medium comprising Non-GRAS ingredients. (SF=serum free; ACF=animal component free).

Provided herein are compositions and methods for the making and using of cell culture medium useful for the culturing of cell-based meat (interchangeable referred to throughout as the slaughter-free meat of the disclosure).

Before describing particular embodiments in detail, it is to be understood that the disclosure is not limited to the particular embodiments described herein, which can vary. It is also to be understood that the terminology used herein is for the purpose of describing particular illustrative embodiments only and is not intended to be limiting unless otherwise defined. The terms used in this specification generally have their ordinary meaning in the art, within the context of this disclosure and in the specific context where each term is used. Certain terms are discussed below or elsewhere in the specification, to provide additional guidance to the practitioner in describing the compositions and methods of the disclosure and how to make and use them. The scope and meaning of any use of a term will be apparent from the specific context in which the term is used. As such, the definitions set forth herein are intended to provide illustrative guidance in ascertaining particular embodiments of the disclosure, without limitation to particular compositions or biological systems.

Standard techniques may be used for recombinant DNA, tissue culture, and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery.

As used in the present disclosure and the appended claims, the singular forms "a," "an" and "the" include plural references unless the content clearly dictates otherwise.

Throughout the present disclosure and the appended claims, unless the context requires otherwise, the word "comprise," or variations such as "comprises" or "comprising," will be understood to imply the inclusion of a stated element or group of elements but not the exclusion of any other element or group of elements.

As used in the present disclosure the term "about" shall generally mean an acceptable degree of error for the quantity measured. Exemplary degrees of error are within 20%, within 10%, and within 5% of a value or range of values.

The term "slaughter" as applied to the manner in which conventional meat is obtained covers all methods traditionally used to kill an animal, with the purpose of directly harvesting its meat for dietary consumption.

The term "slaughter-free" as applied to the cell-based meat products of the present disclosure refers to the process by which the meat is generated, starting with cells in culture, and that method which does not involve the slaughter of an animal in order to directly obtain meat from that animal for dietary consumption. It is understood that in some embodiments, it is possible that the starting cells for use in the cell culture methods may have been obtained following the slaughter of an animal, or a biopsy—although the starting cells for use in culture may have been obtained in this manner, the meat resulting from the culturing of cells, by harvest and a possible subsequent formulation are still considered to be meat obtained in a slaughter-free manner. It is noted that as a general matter, as used herein, harvesting of the slaughter-free cell-based meat product may involve using a buffered solution of water (or other aqueous solution) to remove the meat where it is grown (e.g. the surface of a bioreactor, or in a container comprising a the cells cultured in suspension), and the meat may then captured in a collection device (e.g. net, sieve, colander). In some embodiments the meat may be harvested by physical methods (such as scraping), enzymatic methods, and/or chemical methods. In some embodiments the meat may be harvested by any of the above-mentioned methods and subsequently rinsed with buffered solutions (or other aqueous solutions).

The phrases "cell-based meat", "slaughter-free meat" "slaughter-free cell-based meat", "in vitro produced meat", "in vitro cell-based meat", "cultured meat", "slaughter-free cultured meat", "in vitro produced cultured meat", "in vitro meat", "in vitro cultured meat" and other similar such phrases are interchangeably used herein, and refer to the meat that is generated in vitro, starting with cells in culture, and that method which does not involve the slaughter of an animal in order to directly obtain meat from that animal for dietary consumption.

The phrases "cell culture media", "nutrient media", "cell media", "culture media", "broth", "feed" and other similar phrases are interchangeably used herein. "Nutrient media", as used herein, is in the context of production of cell-based meat starting with cells in culture.

Slaughter-Free Cell-Based Meat

The slaughter-free cell-based meat products of the disclosure are produced by the in vitro culturing of naturally occurring, genetically engineered, or modified animal cells in culture.

The methods provided herein are applicable to any metazoan cell in culture. Generally, the cells are from any metazoan species whose tissues are suitable for dietary consumption. In some embodiments the cells may demonstrate a capacity for differentiation into mature tissue, such as skeletal muscle tissue, other muscle tissues, or any cell, cellular bio-mass, and/or tissue that can be consumed as meat. The cells used in the methods of the present disclosure can be primary cells, or cell lines.

In some embodiments, the cells are derived from any non-human animal species intended for human or non-human dietary consumption (e.g. cells of avian, ovine, caprine, porcine, bovine, piscine origin) (e.g. cells of livestock, poultry, avian, game, or aquatic species).

In some embodiments, the cells are from livestock such as domestic cattle, pigs, sheep, goats, camels, water buffalo, rabbits and the like. In some embodiments, the cells are from poultry such as domestic chicken, turkeys, ducks, geese, pigeons and the like. In some embodiments, the cells are from game species such as wild deer, gallinaceous fowl, waterfowl, hare and the like. In some embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like.

In some embodiments, the cells are from exotic, conserved or extinct animal species. In some embodiments, the cells are from *Gallus gallus, Gallus domesticus, Bos taurus, Sous scrofa, Meleagris gallopavo, Anas platyrynchos, Salmo salar, Thunnus thynnus, Ovis aries, Coturnix coturnix, Capra aegagrus hircus,* or *Homarus americanus*. Accordingly, exemplary cell-based meat products of the disclosure include avian meat products, chicken meat products, duck meat products, and bovine meat products.

In some embodiments, the cells are primary stem cells, self-renewing stem cells, embryonic stem cells, pluripotent stem cells, induced pluripotent stem cells, or transdifferentiated pluripotent stem cells.

In some embodiments, the cells are modifiable by a genetic switch to induce rapid and efficient conversion of the cells to skeletal muscle tissue, connective tissue, fat tissue, and/or any other mature tissue for cultured meat production.

In some embodiments, the cells are myogenic cells, destined to become muscle, or muscle-like cells. In some embodiments, the myogenic cells are natively myogenic, e.g. myoblasts. Natively myogenic cells include, but are not limited to, myoblasts, myocytes, satellite cells, side population cells, muscle derived stem cells, mesenchymal stem cells, myogenic pericytes, or mesoangioblasts.

In some embodiments, cells are of the skeletal muscle lineage. Cells of the skeletal muscle lineage include myoblasts, myocytes, and skeletal muscle progenitor cells, also called myogenic progenitors that include satellite cells, side population cells, muscle derived stem cells, mesenchymal stem cells, myogenic pericytes, and mesoangioblasts.

In other embodiments, the cells are not natively myogenic (e.g. are non-myogenic cells such as fibroblasts or non-myogenic stem cells that are cultured to become myogenic cells in the cultivation infrastructure).

In some embodiments, the cells of the cellular biomass are somatic cells. In some embodiments, the cells of the cellular biomass are not somatic cells.

In some embodiments, the cells comprise a mixture of cell populations described herein, e.g. a mixture of fibrogenic cells and myogenic cells in co-culture, e.g. a mixture of fibroblasts and myoblasts in co-culture. In some embodiments the cells used for the production of cell-based meat are a mixture of fibroblasts and myoblasts in a suspension co-culture. In some embodiments the cells used for the production of cell-based meat are a mixture of fibroblasts and myoblasts in an adherent co-culture. In some embodiments cells in co-culture comprise additional cell types such as adipocytes, endothelial cells, and generally cells from the mesoderm lineage.

In some co-culture embodiments, the cells are in a suspension co-culture, in some embodiments, the cells are in an adherent co-culture, and in some embodiments, the culturing processing makes use of both techniques. The co-cultures provide herein comprise a mixture of at least fibroblasts and myoblasts. In some embodiments, the ratio of the fibroblasts to myoblasts (designated as F and M) ranges from about 5F:95M to about 95F:5M. In exemplary embodiments, the ratio of the fibroblasts to myoblasts is about 5F:95M, 10F:90M, 15F:85M, 20F:80M, 25F:75M, 30F:70M, 35F:65M, 40F:60M, 45F:55M, 50F:50M, 55F:45M, 60F:40M, 65F:35M, 70F:30M, 75F:25M, 80F:20M, 85F:15M, 90F:10M, or even about 95F:5M.

In some embodiments, the cells are non-myogenic, and such non-myogenic cells can be programmed to be myogenic, for example the cells may comprise fibroblasts modified to express one or more myogenic transcription factors. In exemplary embodiments, the myogenic transcription factors include MYOD1, MYOG, MYF5, MYF6, PAX3, PAX7, paralogs, orthologs, and genetic variants thereof. In some embodiments, the cells are modified to express one or more myogenic transcription factors as described in a PCT publication, WO/2015/066377, incorporated by reference herein in its entirety.

In some embodiments, the cells are genetically modified to inhibit a pathway, e.g. the HIPPO signaling pathway. Exemplary methods to inhibit the HIPPO signaling pathway as described in a PCT Application No. PCT/US2018/031276, incorporated by reference herein in its entirety.

In some embodiments, the cells are modified to express telomerase reverse transcriptase (TERT) and/or inhibit cyclin-dependent kinase inhibitors (CKI). In some embodiments, the cells are modified to express TERT and/or inhibit cyclin-dependent kinase inhibitors as described in a PCT publication, WO 2017/124100, incorporated by reference herein in its entirety.

In some embodiments, the cells are modified to express glutamine synthetase (GS), insulin-like growth factor (IGF), and/or albumin. Exemplary methods of modifying cells to express GS, IGF, and/or albumin are described in a PCT Application No. PCT/US2018/042187 which is incorporated by reference herein in its entirety.

In some embodiments, the cell-based meat product has various characteristics. Exemplary characteristics of the cell-based meat are described in U.S. application Ser. No. 17/033,635 and PCT Application No. PCT/US2021/016681, which are incorporated by reference herein in its entirety.

In some embodiments the cells are genetically edited, modified, or adapted to grow without the need of specific ingredients including specific amino acids, carbohydrates, vitamins, inorganic salts, trace metals, TCA cycle intermediates, lipids, fatty acids, supplementary compounds, growth factors, adhesion proteins and recombinant proteins.

In some embodiments, the cells may comprise any combinations of the modifications described herein.

The cell-based meat of the present disclosure, generated using the cell media formulations provided herein, is suitable for both human and non-human consumption. In some embodiments, the cell-based meat is suitable for consumption by animals, such as domesticated animals. Accordingly, the cell media formulations provided herein support the growth of "pet food", e.g. dog food, cat food, and the like.

Cell Culture Media Formulations

Provided herein are nutrient media formulations and related compositions and methods, useful for the culturing and production of slaughter-free meat.

Safety for use in the production of meat intended for consumption is one of the many advantages of the cell culture media of the present disclosure. In some embodiments the cell culture media is itself edible, e.g. does not cause any deleterious effects if ingested. The media formulations provided herein generally comprise ingredients that are each individually or in combination edible, (e.g. safe to consume, food-grade, food-safe, food-quality, food-acceptable, food-compatible, food-category, foodstuff, for food use, eatable, comestible). Production of media formulations of the disclosure is achieved by engineering the media formulation to include ingredients that are inherently safe and/or customizing the concentrations of ingredients to be provided at safe levels, as determined by any one or more of the standards discussed below.

In some embodiment an edible nutrient medium for the production of slaughter-free meat comprises a plurality of ingredients, wherein each ingredient is approved for use in food and/or is at or below its ADI value. In some embodiments an intermediate version of the cell culture medium may or may not be edible. In some embodiments the cell culture medium comprises a plurality of ingredients wherein one or more ingredient is approved for use in food. In some embodiments the cell culture medium comprises a plurality of ingredients wherein each ingredient is approved for use in food. As used in the present disclosure, an ingredient "approved for use in food" refers to an ingredient that is approved for use in food by a widely accepted standard, e.g. a nationally or internationally accepted standard. These standards include, but are not limited to, standards set forth by regulatory bodies such as the Food and Drug Administration (FDA), the United States Department of Agriculture (USDA), the World Health Organization (WHO), the United Nations Food and Agriculture Organization (FAO), and the European Food Safety Authority (EFSA).

Accordingly, in some embodiments, the cell culture media of the present disclosure may comprise ingredients approved for use in food that are recognized by the FDA as Generally Recognized As Safe (GRAS). In some embodiments the cell culture media comprises ingredients that are GRAS certified ingredients, Non-GRAS certified ingredients, or mixtures thereof. In certain embodiments the cell culture media comprises only GRAS certified ingredients. As the list of GRAS substances is updated by the FDA, the GRAS certified ingredients that may be used in the formulation of the cell culture medium may be modified. In some embodiments the cell culture media comprise ingredients with a currently unknown GRAS status. It is contemplated the media provided herein may comprise an ingredient that may currently have an unknown GRAS status or a Non-GRAS status, but in the future may be GRAS certified.

In some embodiments the cell culture media of the present disclosure may comprise ingredients approved for use in food as recognized by the FDA.

In some embodiments the cell culture media of the present disclosure may comprise ingredients approved for use in food as recognized by the USDA.

In some embodiments the cell culture media of the present disclosure may comprise ingredients approved for use in food as recognized by the FAO.

In some embodiments the cell culture media of the present disclosure may comprise ingredients approved for use in food as recognized by the WHO.

In some embodiments the cell culture media of the present disclosure may comprise ingredients approved for use in food as recognized by the FAO and the WHO in the *Codex alimentarius*.

In some embodiments the cell culture media of the present disclosure may comprise ingredients approved for use in food as recognized by the EFSA.

In some embodiments the cell culture media of the present disclosure may comprise ingredients approved for use in food as recognized by the Food Chemicals *Codex* (FCC).

In some embodiments the cell culture media comprises ingredients formulated at or below a safe concentration for consumption by humans and/or domesticated animals. In some embodiments, ingredients in the media may be deemed to be at a safe concentration for consumption by humans and/or domesticated animals if the theoretical maximum amount of the compound in the meat product is at or below the Average Daily Intake (ADI) level. The average daily intake (ADI) is conventionally determined as a result of a safety factor of 100-fold below the experimentally derived No Observable Adverse Effect Limits (NOAEL) for an appropriate animal species for sub-chronic or acute exposure. A skilled artisan in the field would understand how to compute the NOAEL value. For example, the FDA defines NOAEL as the highest dose level that does not produce a significant increase in adverse effects in comparison to the control group. The ADI is determined in an appropriately sensitive species, usually rodent, and it is reported as mg of substance/kg of animal body weight/24-hour period. Calculating the maximum theoretical concentration of each media compound in the final product is done by assuming 100% incorporation of the compound from the media into the product.

In some embodiments the cell culture medium comprises a plurality of ingredients wherein one or more ingredients is at or below its Average Daily Intake (ADI) value. In some embodiments the cell culture medium comprises a plurality of ingredients wherein each ingredient is at or below its ADI value. In some embodiments, the cell culture medium comprises a plurality of ingredients, wherein each ingredient is approved for use in food and/or is at or below its ADI value.

In some embodiments the cell culture media comprises ingredients currently not approved for use in food and/or ingredients currently having an unknown status for use in food. In some embodiments ingredients currently not approved for use in food are formulated at or below their ADI value.

In some embodiments the cell culture media comprises a combination of at least one ingredient approved for use in food and at least one ingredient currently not approved for use in food. In some embodiments the cell culture media comprises a combination of at least one ingredient approved for use in food and at least one ingredient currently not approved for use in food, wherein each ingredient is formulated at or below its ADI value.

In some embodiments the cell culture media comprises ingredients approved for use in food formulated at a concentration at or above its ADI value. In some embodiments the cell culture media comprises ingredients currently not approved for use in food formulated at a concentration at or above its ADI value. In some embodiments the cell culture media comprises a combination of at least one ingredient approved for use in food and at least one ingredient currently not approved for use in food, wherein each ingredient is formulated at or above its ADI values.

Figure 1B:
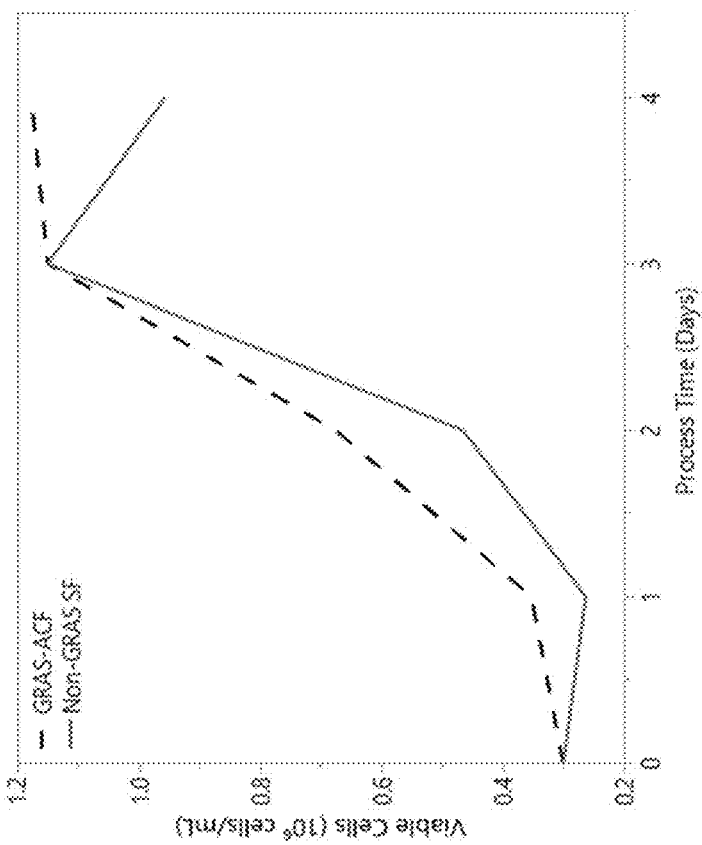
FIG. 1B shows a comparison of the growth of suspension *Gallus* cells cultured in a medium comprising GRAS ingredients vs. growth in a medium comprising Non-GRAS ingredients.
Figure 2:
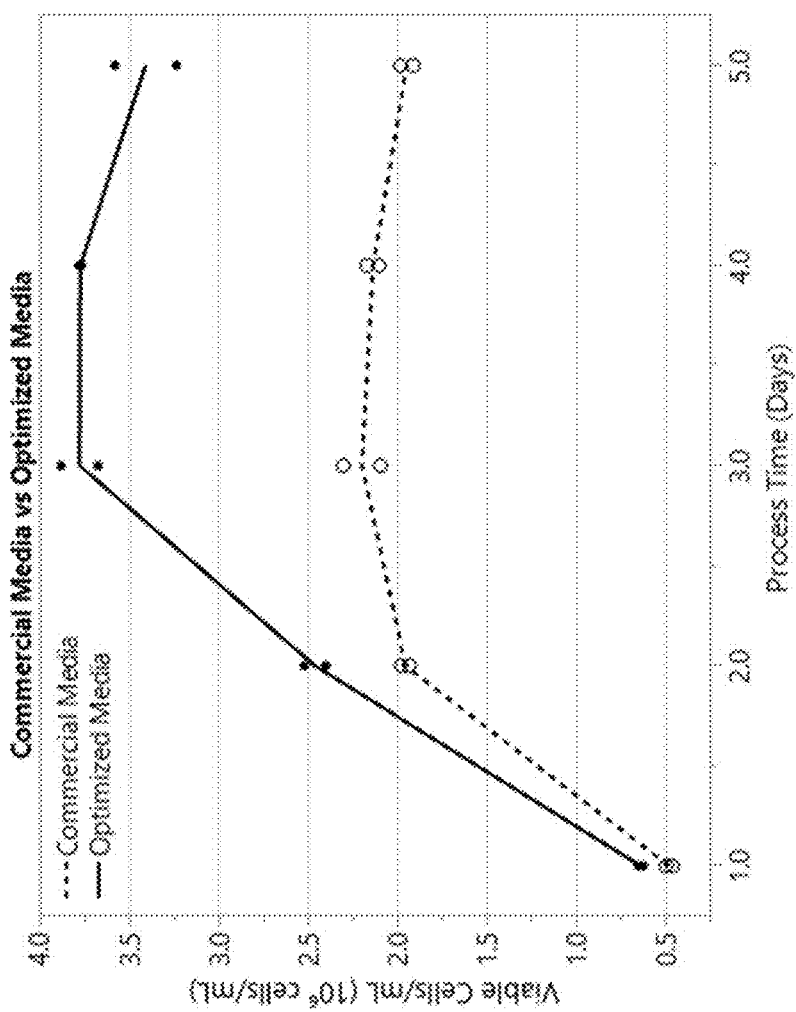
FIG. 2 shows a comparison of the growth of suspension *Gallus* cells cultured in a commercial medium vs. growth in an optimized medium.

As shown in FIG. 1A-B and detailed in Examples 1-2 below, exemplary safe cell culture media of the present disclosure comprising only GRAS ingredients and lacking animal-derived components showed a higher growth rate of both adherent and suspension cells, when compared to cell culture media containing potentially hazardous Non-GRAS ingredients. FIG. 2, detailed in Example 3 below, compares the growth of suspension cells in an exemplary optimized serum-free medium of the present disclosure comprising only GRAS ingredients with a commercial medium. The optimized medium showed enhanced performance in cell viability.

Another advantage of the cell culture media of the present disclosure is the absence of animal-derived serum and other animal-derived components in the cell culture media which can impart contamination, batch-to-batch variability, microbial contamination, increase cost, and required additional quality control measures. The safe culture media formulations provided herein may be optimized to support the culture of a wide variety of cells in different cultivation formats, which is a challenging task in the absence of the nutrients commonly relied on from animal-derived serum. Accordingly, the cell culture media provided herein allow for the efficient culturing of cells under conditions of reduced animal-derived serum concentrations, or even in the absence of animal-derived serum entirely. In some embodiments, the cell culture medium comprises no more than 10%, 9%, 8%, 7%, 6%, 5%, 4%, 3%, 2%, 1%, 0.5%, 0.1%, 0.05% or no more than 0.01% animal-derived serum. In some embodiments the cell culture medium is substantially free of animal-derived serum. Substantially free refers to an amount of animal-derived serum present at or below level of detection. A skilled artisan would know how to determine a level of detection. For example, the level of detection may be determined by mass spectrometry-based techniques, PCR-based techniques, antibody-based techniques, ELISA-based techniques, HPLC-based techniques, and other well-known chemical or biological detection methods. In some embodiments, the cell culture medium is free of animal-derived serum.

In some embodiments the cell culture medium comprises non-animal derived serum. Examples of non-animal derived serum include synthetic serum, serum substitutes, serum replacements, chemically defined serum, KnockOut™ Serum Replacement, and SigMatrix Serum diluent. In some embodiments, the cell culture medium comprises no more than 10%, 9%, 8%, 7%, 6%, 5%, 4%, 3%, 2%, 1%, 0.5%, 0.1%, 0.05% or 0.01% non-animal derived serum. In some embodiments the cell culture medium is substantially free of non-animal derived serum. Substantially free refers to an amount of non-animal derived serum present at or below level of detection. A skilled artisan would know how to determine a level of detection. For example, the level of detection may be determined by mass spectrometry-based techniques, PCR-based techniques, antibody-based techniques, ELISA-based techniques, HPLC-based techniques, and other well-known chemical or biological detection methods. In some embodiments, the cell culture medium is free of non-animal derived serum.

Likewise, provided herein a cell culture medium provided herein comprises no more than 10%, 9%, 8%, 7%, 6%, 5%, 4%, 3%, 2%, 1%, 0.5%, 0.1%, 0.05% or no more than 0.01% animal-derived components (including but not limited to animal-derived serum). In some embodiments the cell culture medium is substantially free of animal-derived components. Substantially free refers to an amount of an animal-derived component present at or below level of detection. A skilled artisan would know how to determine a level of detection. For example, the level of detection may be determined by mass spectrometry-based techniques, PCR-based techniques, antibody-based techniques, ELISA-based techniques, HPLC-based techniques, and other well-known chemical or biological detection methods. In some embodiments, the cell culture medium is free of animal-derived components.

The cell culture media of the present disclosure are customizable and modular. The ingredients of the media formulation may be customized to the specific type of cell-based meat being produced for optimal results. For example, for culturing chicken cells the media may comprise proteins, such as growth factors, that are also derived from chicken. Similarly, a media for culturing bovine cells may comprise proteins of only bovine origin. In some embodiments, the media for culturing chicken cells may comprise proteins, such as growth factors, of bovine origin. In some embodiments, the media may comprise a universal protein, such as a universal growth factor, for culturing any type of cell-based meat.

The cell-based meat produced by the cell culture media of the present disclosure may be equivalent or comparable to traditional meat obtained by slaughter. The cell culture media of the present disclosure allow for production of cell-based meat that is equivalent to its traditionally obtained counterparts in all respects, such as flavor, thickness, firmness, composition, etc. For example, riboflavin, a vitamin and cofactor, when added into the cell culture media increases fatty acid synthesis in the cells in culture. Accordingly, the levels of riboflavin in the cell culture media may be tuned such that the fatty acid content of the final cell-based meat matches that of traditional meat, and thus matching the flavor to equivalent traditional meat. In some embodiments the cell culture media comprises riboflavin. In some embodiments the cell culture media comprises galactose, uridine, and manganese (GUM).

The cell culture media of the present disclosure enable modulation of standard of identity (SOI) performance factors of the cell-based meat produced therefrom. Optimization of media components may be used to tune performance factors, such as to maintain cell viability, maximize the biomass/yield, tune the flavor/taste, and/or achieve desired tissue characteristics of the cell-based meat (thickness, firmness, etc.). In some embodiments the performance factor is cell viability. In some embodiments the performance factor is cell growth. In some embodiments the performance factor is biomass or yield of the final cell-based meat product. In some embodiments the performance factor is the taste or flavor of the cell-based meat. In some embodiments the performance factor is quality of the cell-based meat measured for instance in terms of tissue firmness, thickness, etc.

In some embodiments the performance factors are improved in cell-based meat produced by the cell culture media of the present disclosure as compared to cell-based meat produced by conventional media. In some embodiments the performance factors are improved in cell-based meat produced by the cell culture media of the present disclosure as compared to cell-based meat produced by media containing Non-GRAS ingredients. In some embodiments the performance factors are improved in cell-based meat produced by the cell culture media of the present disclosure as compared to cell-based meat produced by conventional media absent any ingredient that is not approved for use in food and/or is above its ADI value.

In some embodiments the cell viability is improved by at least 50%, 55%, 60%, 65%, 70%, 75%, 80%, 85%, 90%, 95%, or 99% by culturing the cells in the cell culture media of the present disclosure as compared to culturing in conventional media. In some embodiments the cell viability is improved by at least 50%, 55%, 60%, 65%, 70%, 75%, 80%, 85%, 90%, 95%, or 99% by culturing the cells in the cell culture media of the present disclosure as compared to culturing in media containing Non-GRAS ingredients.

In some embodiments the cell growth rate is improved by at least 50%, 55%, 60%, 65%, 70%, 75%, 80%, 85%, 90%, 95%, or 99% by culturing the cells in the cell culture media of the present disclosure as compared to culturing in conventional media. In some embodiments the cell growth rate is improved by at least 50%, 55%, 60%, 65%, 70%, 75%, 80%, 85%, 90%, 95%, or 99% by culturing the cells in the cell culture media of the present disclosure as compared to culturing in media containing Non-GRAS ingredients.

In some embodiments the final biomass/yield of the cell-based meat is improved by at least 50%, 55%, 60%, 65%, 70%, 75%, 80%, 85%, 90%, 95%, or 99% by producing the cell based meat in the cell culture media of the present disclosure as compared to conventional media. In some embodiments the final biomass/yield of the cell-based meat is improved by at least 50%, 55%, 60%, 65%, 70%, 75%, 80%, 85%, 90%, 95%, or 99% by producing the cell based meat in the cell culture media of the present disclosure as compared to media containing Non-GRAS ingredients.

Yet another advantage of the cell culture media of the present disclosure is their rapid application and formulation at any desired scale at low cost. For example, they are applicable in batch, fed-batch, chemostat, perfusion, and/or intensified bioreactor tissue cultivator processes.

In some embodiments the cell culture medium is chemically defined, i.e. a media in which all the ingredients and their concentrations are known. In some embodiments there may be a need to use a chemically defined, animal-component free medium to minimize any potential contaminants and decrease lot-to-lot variability while maintaining high cell growth, cultured meat production, and matching the similarity of these cell-based meat to the standard of identity of the conventional meat product. For example, many traditional cell culture media use animal derived oils, such as cod liver oil as a lipid source, as there are many methyl ester fatty acids in cod liver oil. However, cod liver oil does not allow control of the fatty acid composition of the cell-based meat and may give erroneous fatty acid profiles, e.g. chicken that has a fish profile. In some embodiments, the cell culture medium does not contain any undefined ingredients, such as hydrolysates, undefined serum replacements and animal-based oils (e.g. cod liver oil). In some embodiments provided herein are plant-derived food oils and/or synthetically derived fatty lipids to provide ideal ratios to achieve desired fatty acid profiles. In some embodiments, the cell culture medium does not contain dyes, such as pH indicator dyes (e.g. phenol red). Phenol red is commonly found in classical cell culture media (such as Ham's F12 and DMEM) as a colorimetric pH indicator. It bears structural resemblance to some nonsteroidal estrogens. Estrogens are considered hormones and not approved for use in food.

In some embodiments the cell culture medium may comprise undefined non-animal derived ingredients, such as plant hydrolysates.

Amino Acids

The cell culture media comprise one or more amino acids. The amino acids may be of either L stereochemistry, D stereochemistry, or in a combination of L and D isomers such as in the form of a racemate. In exemplary embodiments, the amino acids are of L stereochemistry. In some embodiments the amino acids comprise the twenty naturally occurring canonical amino acids.

Examples of amino acids included in the media of the disclosure include alanine, arginine, aspartic acid, asparagine, cysteine, cystine, glutamic acid, glutamine, glycine, histidine, proline, hydroxyproline, isoleucine, leucine, lysine, methionine, phenylalanine, serine, threonine, tryptophan, tyrosine, valine, and ornithine.

In some embodiments the cell culture media comprise one or more essential amino acids, non-essential amino acids, proteinogenic amino acids, non-proteinogenic amino acids, and/or branched chain amino acids.

In some embodiments the cell culture media comprise one or more unnatural amino acids, amino acids analogs, amino acid derivatives, beta-amino acids, gamma amino acids, amino acid mimetics, and/or oligopeptides. In some embodiments the cell culture media comprise taurine, carnosine, alpha-aminobutyric acid, beta-aminobutyric acid, and gamma-aminobutyric acid.

In some embodiments the cell culture media comprise one or more amino acids in the concentration range shown in Table 1 below. For this and other tables of the disclosure, the ranges are inclusive of the recited lowest and highest concentrations.

TABLE 1

Exemplary amino acids and related compounds

| Exemplary Amino Acids and Related Compounds | Lowest Concentration (g/L) | Highest Concentration (g/L) |
| --- | --- | --- |
| L-ALANINE | 0.0001 | 0.5 |
| L-ARGININE | 0.01 | 2.5 |
| L-ARGININE HYDROCHLORIDE | 0.01 | 1 |
| L-ASPARAGINE ANHYDROUS | 0.1 | 1.5 |
| L-ASPARAGINE MONOHYDRATE | 0.01 | 0.9 |
| L-CYSTEINE HYDROCHLORIDE | 0.001 | 0.5 |
| L-CYSTINE DIHYDROCHLORIDE | 0.005 | 1.5 |
| L-GLUTAMIC ACID | 0.01 | 1.5 |
| L-GLUTAMIC ACID MONOSODIUM SALT MONOHYDRATE | 0.01 | 1.5 |
| L-GLUTAMINE | 0.14 | 1.5 |
| L-GLYCINE | 0.01 | 0.5 |
| L-HISTIDINE FREE BASE | 0.01 | 0.5 |
| L-HISTIDINE HYDROCHLORIDE | 0.01 | 0.5 |
| HYDROXY-L-PROLINE | 0.01 | 0.25 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-SERINE | 0.1 | 1 |
| L-THREONINE | 0.05 | 0.5 |
| L-TRYPTOPHAN | 0.01 | 0.5 |
| L-TYROSINE DISODIUM SALT DIHYDRATE | 0.01 | 0.5 |
| L-VALINE | 0.1 | 0.75 |
| L-ORNITHINE | 0.001 | 0.05 |
| L-ASPARTIC ACID | 0.1 | 0.8 |
| L-ALPHA-AMINOBUTYRIC ACID | 0.001 | 0.025 |
| GAMMA-AMINOBUTYRIC ACID | 0.01 | 0.2 |
| L-CARNOSINE | 0.01 | 1 |

Carbohydrates

In some embodiments the cell culture media comprise one or more carbohydrates. The carbohydrates may comprise monosaccharides, disaccharides, oligosaccharides, polysaccharides, and/or polyols. Examples of carbohydrates include glucose, galactose, mannose, maltose, fucose, sucrose, fructose, allose, altrose, gulose, idose, talose, psicose, sorbose, tagatose, lactose, ribose and myo-inositol.

In some embodiments the cell culture media comprise carbohydrate derivatives and/or synthetic carbohydrates.

Examples include amino sugars, reduced sugars, oxidized sugars, artificial sugars, deoxy sugars, gluconic acid, glucuronic acid, glucaric acid, glycerol, glucosamine, galactosamine, mannosamine, fucose, and deoxyribose.

In some embodiments the cell culture media comprise one or more carbohydrates in the concentration range shown in Table 2 below.

TABLE 2

Exemplary carbohydrates and related compounds

| Exemplary Carbohydrates and Related Compounds | Lowest Concentration (g/L) | Highest Concentration (g/L) |
| --- | --- | --- |
| D-GLUCOSE | 1 | 12 |
| GALACTOSE | 0.1 | 2 |
| MANNOSE | 0.1 | 2 |
| MALTOSE | 0.1 | 2 |
| FUCOSE | 0.1 | 2 |
| SUCROSE | 0.1 | 12 |
| FRUCTOSE | 0.1 | 2 |
| ALLOSE | 0.1 | 2 |
| ALTROSE | 0.1 | 2 |
| GULOSE | 0.1 | 2 |
| IDOSE | 0.1 | 2 |
| TALOSE | 0.1 | 2 |
| PSICOSE | 0.1 | 2 |
| SORBOSE | 0.1 | 2 |
| TAGATOSE | 0.1 | 2 |
| LACTOSE | 0.1 | 2 |
| MYO-INOSITOL | 0.01 | 0.25 |
| RIBOSE | 0.1 | 2 |

Vitamins

In some embodiments the cell culture media comprise one or more vitamins. Examples of vitamins include vitamin C, vitamin B1, vitamin B2, vitamin B7, vitamin D, vitamin B9, vitamin B3, vitamin B5, vitamin B6, vitamin B12, vitamin E.

In some embodiments the cell culture media comprise vitamin precursors, intermediates, and metabolites. Examples include, niacinamide, menadione, choline chloride, and para-amino benzoic acid.

In some embodiments the cell culture media comprise vitamins in the concentration range shown in Table 3 below.

TABLE 3

Exemplary vitamins and related compounds

| Exemplary Vitamins and Related Compounds | Lowest Concentration (g/L) | Highest Concentration (g/L) |
| --- | --- | --- |
| ASCORBIC ACID (Vit C) | 0.0001 | 0.5 |
| D-BIOTIN (Vit B7) | 1.00E−06 | 0.005 |
| ERGOCALCIFEROL (Vit D2) | 1.00E−06 | 5.00E−05 |
| FOLIC ACID (Vit B9) | 0.0015 | 0.02 |
| MENADIONE (Vit K3) | 0.00001 | 0.0005 |
| NIACINAMIDE (NICOTINAMIDE) (Vit B3) | 0.001 | 0.01 |
| NIACIN (Vit B3) | 1.00E−06 | 5.00E−02 |
| CALCIUM D-PANTOTHENATE (Vit B5) | 0.0005 | 0.01 |
| PYRIDOXINE HYDROCHLORIDE (Vit B6) | 1.00E−05 | 0.01 |
| RIBOFLAVIN (Vit B2) | 0.0001 | 0.005 |
| THIAMINE HCL (Vit B1) | 0.0025 | 0.05 |
| CYANOCOBALAMIN (Vit B12) | 1.00E−05 | 0.005 |
| DL-ALPHA-TOCOPHEROL (Vit E) | 1.00E−07 | 0.002 |
| D-ALPHA-TOCOPHEROL (Vit E) | 1.00E−07 | 0.002 |
| PARA-AMINO BENZOIC ACID (PABA) | 0.001 | 0.01 |

TABLE 3-continued

Exemplary vitamins and related compounds

| Exemplary Vitamins and Related Compounds | Lowest Concentration (g/L) | Highest Concentration (g/L) |
| --- | --- | --- |
| PYRIDOXAL HYDROCHLORIDE (Vit B6) | 0.0005 | 0.01 |

Inorganic Salts

In some embodiments the cell culture media comprise one or more inorganic salts. Examples of inorganic salts include calcium chloride, sodium chloride, sodium phosphate, magnesium chloride, magnesium sulfate, and potassium chloride.

In some embodiments the cell culture media comprise inorganic salts in the concentration range shown in Table 4 below.

TABLE 4

Exemplary inorganic salts and related compounds

| Exemplary Inorganic Salts and Related Compounds | Lowest Concentration (g/L) | Highest Concentration (g/L) |
| --- | --- | --- |
| CALCIUM CHLORIDE | 0.0005 | 0.2 |
| SODIUM CHLORIDE | 0.1 | 10 |
| SODIUM PHOSPHATE MONOBASIC | 0.01 | 5 |
| SODIUM PHOSPHATE DIBASIC | 0.01 | 5 |
| MAGNESIUM CHLORIDE | 0.0005 | 0.1 |
| MAGNESIUM SULFATE | 0.0005 | 0.1 |
| POTASSIUM CHLORIDE | 0.001 | 1.5 |

Trace Metals

In some embodiments the cell culture media comprise one or more trace metals. Examples of trace metals include cadmium, strontium, copper, selenium, silicon, copper, iron, nickel, and tin. The trace metals may be present in different oxidation states, salts, solvates, and hydrates.

In some embodiments the cell culture media comprise trace metals in the concentration range shown in Table 5 below.

TABLE 5

Exemplary trace metals and related compounds

| Exemplary Trace Metals and Related Compounds | Lowest Concentration (g/L) | Highest Concentration (g/L) |
| --- | --- | --- |
| CADMIUM HEMIPENTAHYDRATE | 0.00000001 | 0.000001 |
| COBALT CHLORIDE | 0.0000001 | 0.00001 |
| AMMONIUM MOLYBDATE | 0.0000001 | 0.0001 |
| SODIUM MOLYBDATE | 0.0000001 | 0.0001 |
| AMMONIUM METAVANADATE | 0.00000001 | 0.000005 |
| SODIUM METAVANADATE | 0.000000001 | 0.000005 |
| STRONTIUM CHLORIDE HEXAHYDRATE | 0.00001 | 0.01 |
| COPPER SULFATE | 2.50E−06 | 0.0025 |
| SODIUM SELENITE | 1.00E−06 | 1.00E−04 |
| SODIUM METASILICATE | 0.00001 | 0.001 |
| CUPRIC CHLORIDE | 1.00E−07 | 0.001 |
| FERRIC AMMONIUM CITRATE | 0.001 | 1 |
| FERROUS SULFATE | 1.00E−05 | 0.001 |
| FERRIC NITRATE | 1.00E−05 | 0.001 |
| NICKEL SULFATE HEXAHYDRATE | 1.00E−07 | 2.00E−06 |
| STANNOUS CHLORIDE DIHYDRATE | 1.00E−07 | 1.00E−06 |
| FERRIC CITRATE | 0.01 | 1 |
| RUBIDIUM CHLORIDE | 1.00E+07 | 5.00E+05 |

Lipids

In some embodiments the cell culture media comprise one or more lipids. Examples of lipids include fatty acids, fats, oils, glycerides, non-glyceride lipids, sphingolipids, glycolipids, phospholipids, sulfolipids, steroids, complex lipids, derived lipids, and lipid mixtures. Examples include oleic acid, linoleic, acid, arachidonic acid, linolenic acid, myristic acid, palmitic acid, palmitoleic acid, stearic acid, and lecithin. In some embodiments the cell culture media comprise food oils and food-grade plant oils. Examples of oils include flaxseed oil, canola oil, and algal oil.

In some embodiments the cell culture media comprise lipids in the concentration range shown in Table 6 below.

TABLE 6

Exemplary lipids, food oils and related compounds

| Exemplary Lipids and Related Compounds | Lowest Concentration (g/L) | Highest Concentration (g/L) |
| --- | --- | --- |
| DL-ALPHA-LIPOIC-ACID | 0.00001 | 0.005 |
| OLEIC ACID | 1.00E−06 | 0.001 |
| CHOLESTEROL | 0.00005 | 0.005 |
| LECITHIN | 1.00E−05 | 0.01 |
| LINOLEIC ACID | 1.00E−05 | 0.005 |
| ARACHIDONIC ACID | 1.00E−08 | 5.00E−05 |
| LINOLENIC ACID | 1.00E−06 | 1.00E−03 |
| MYRISTIC ACID | 1.00E−06 | 1.00E−03 |
| PALMITIC ACID | 1.00E−06 | 1.00E−03 |
| PALMITOLEIC ACID | 1.00E−06 | 1.00E−03 |
| STEARIC ACID | 1.00E−06 | 1.00E−03 |
| FLAXSEED OIL | 1.00E−06 | 5.00E−03 |
| CANOLA OIL | 1.00E−06 | 5.00E−03 |
| ALGAL OIL | 1.00E−06 | 5.00E−03 |
| OTHER FOOD OILS | 1.00E−06 | 5.00E−03 |

TCA Cycle Intermediates

In some embodiments the cell culture media comprise one or more TCA cycle intermediates. Examples of TCA cycle intermediates include pyruvic acid, succinic acid, citric acid, isocitric acid, alpha-ketoglutaric acid, fumaric acid, malic acid, oxaloacetic acid, acetylcholine, acetyl CoA, and succinyl CoA.

In some embodiments the cell culture media comprise TCA cycle intermediates in the concentration range shown in Table 7 below.

TABLE 7

Exemplary TCA cycle intermediates and related compounds

| Exemplary TCA Cycle Intermediates and Related Compounds | Lowest Concentration (g/L) | Highest Concentration (g/L) |
| --- | --- | --- |
| SODIUM PYRUVATE | 0.01 | 0.5 |
| SUCCINIC ACID | 0.005 | 1.5 |
| SODIUM SUCCINATE | 0.005 | 0.1 |

Supplementary Ingredients

In some embodiments the cell culture media comprise one or more supplementary ingredients. Examples of supplementary compounds include Polysorbate 80®, ethanolamine, ethanol, sodium citrate, sodium gluconate, methyl-beta-cyclodextrin, glycolysis intermediates, iron carriers, ferric maltol, ferrous gluconate, shear protectants, polyethylene glycol, antifoaming agents, methyl cellulose, poloxamers, and Simethicone®.

In some embodiments the cell culture media comprise supplementary compounds in the concentration range shown in Table 8 below.

TABLE 8

Exemplary supplementary ingredients

| Exemplary Supplementary Ingredients | Lowest Concentration (g/L) | Highest Concentration (g/L) |
| --- | --- | --- |
| HYPOXANTHINE | 0.0001 | 0.01 |
| THYMIDINE | 1.50E−04 | 0.001 |
| TWEEN 80 (POLYSORBATE) | 1.00E−04 | 0.005 |
| PUTRESCINE DIHYDROCHLORIDE | 1.00E−04 | 0.0009 |
| SPERMINE TETRAHYDROCHLORIDE | 1.00E−02 | 0.05 |
| SPERMIDINE | 1.00E−04 | 0.05 |
| CADAVERINE | 1.00E−04 | 0.05 |
| ETHANOLAMINE | 2.00E−03 | 0.08 |
| ETHANOL (ETHYL ALCOHOL) | 6.00E−05 | 1 |
| SODIUM CITRATE | 0.5 | 0.5 |
| SODIUM GLUCONATE | 0.5 | 1.5 |
| METHYL BETA CYCLODEXTRIN | 0.05 | 0.075 |
| L-TAURINE | 0.01 | 0.1 |
| CHOLINE CHLORIDE | 0.001 | 0.5 |

In some embodiments, the cell culture media comprises a core set of ingredients, depending on the properties of the cell culture as desired. In exemplary embodiments the core ingredients of the cell culture media include at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four or more of L-arginine, L-cysteine, L-cystine, L-glutamine, L-histidine, L-isoleucine, L-leucine, L-lysine, L-methionine, L-phenylalanine, L-proline, L-tryptophan, L-tyrosine, L-valine, D-glucose, niacin, riboflavin, ergocalciferol, ascorbic acid, copper salts, sodium salts, iron salts, magnesium salts, and zinc salts.

In exemplary embodiments the core ingredients of the cell culture media include at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four or more of L-arginine, L-cysteine, L-cystine, L-glutamine, L-histidine, L-isoleucine, L-leucine, L-lysine, L-methionine, L-phenylalanine, L-proline, L-tryptophan, L-tyrosine, L-valine, D-glucose, niacin, riboflavin, ergocalciferol, ascorbic acid, copper sulfate, sodium selenite, ferric ammonium citrate, magnesium chloride, magnesium sulfate, and zinc sulfate.

In other embodiments the cell culture media comprises L-arginine, L-cysteine, L-cystine, L-glutamine, L-histidine, L-isoleucine, L-leucine, L-lysine, L-methionine, L-phenylalanine, L-proline, L-tryptophan, L-tyrosine, L-valine, D-glucose, niacin, riboflavin, ergocalciferol, ascorbic acid, copper sulfate, sodium selenite, ferric ammonium citrate, magnesium chloride, magnesium sulfate, and zinc sulfate.

In some embodiments the cell culture media comprise at least the ingredients shown in Table 9 below.

TABLE 9

Exemplary ingredients

| Exemplary Ingredients | Lowest Concentration (g/L) | Highest Concentration (g/L) |
|---|---|---|
| L-ARGININE | 0.01 | 2.5 |
| L-CYSTEINE | 0.001 | 0.5 |
| L-CYSTINE | 0.005 | 1.5 |
| L-GLUTAMINE | 0.14 | 1.5 |
| L-HISTIDINE | 0.01 | 0.5 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-TRYPTOPHAN | 0.01 | 0.5 |
| L-TYROSINE | 0.01 | 0.5 |
| L-VALINE | 0.1 | 0.75 |
| D-GLUCOSE | 1 | 12 |
| NIACIN (Vit B3) | 1.00E−06 | 5.00E−02 |
| RIBOFLAVIN | 0.0001 | 0.005 |
| ERGOCALCIFEROL (VitD2) | 1.00E−06 | 5.00E−05 |
| ASCORBIC ACID (Vit C) | 0.0001 | 0.5 |
| COPPER SULFATE | 2.50E−06 | 0.0025 |
| SODIUM SELENITE | 1.00E−06 | 1.00E−04 |
| FERRIC AMMONIUM CITRATE | 0.001 | 1 |
| MAGNESIUM CHLORIDE | 0.0005 | 0.1 |
| MAGNESIUM SULFATE | 0.0005 | 0.1 |
| ZINC SULFATE | 0.00005 | 0.01 |

Salts, solvates, hydrates, polymorphs, anhydrates, esters, isomers, metabolites, precursors, derivatives and prodrugs of any of the cell culture medium ingredients disclosed in the present disclosure may be utilized.

Growth Factors

In some embodiments the cell culture media comprise one or more growth factors. The growth factors may be produced by a variety of methods known in the art. The growth factors may comprise a sequence that is either naturally occurring or non-naturally occurring. For example, a growth factor comprising a non-naturally occurring sequence may be a variant of a naturally existing sequence. Alternatively, a growth factor comprising a non-naturally occurring sequence may not resemble the naturally occurring counterpart with much sequence similarity but retain similar function. The growth factors may be produced by a variety of methods known in the art, for example the growth factor may be recombinantly produced, isolated and purified or chemically synthesized. The growth factors of the present disclosure encompass homologs, orthologs and paralogs. Examples of growth factors that may be included in the media provided herein include Fibroblast Growth Factor, Fibroblast Growth Factor 1 (FGF-1), Fibroblast Growth 2 Factor (FGF-2), Platelet-derived Growth Factor, Platelet-derived Growth Factor subunit A (PDGF-A), Platelet-derived Growth Factor subunit B (PDGF-B), Platelet-derived Growth Factor-AA (PDGF-AA), Platelet-derived Growth Factor-BB (PDGF-BB), Insulin like Growth Factor 1 (IGF-1), Long arginine 3-IGF-1 (LR3-IGF1), Insulin, Transferrin, Serotransferrin, Ovotransferrin, Connective Tissue Growth Factor (CTGF), Epidermal growth factor (EGF), Transforming Growth Factor (TGF), Transforming growth factor Beta (TGF-β), Bone morphogenetic proteins (BMP), Hepatocyte Growth Factor (HGF), WNT proteins, WNT 1, WNT 11, WNT 11B, Myogenic regulatory factors, Myogenic factor 6, Interleukins, IL2, IL2 isoform X1, IL6, IL6 precursor, Leukemia inhibitory factor (LIF), LIF isoform X1 IL3, vascular endothelial growth factor (VEGF), variants, thermostable variants, precursors, isoforms, homologs, paralogs, orthologs, and biologically active fragments thereof. Exemplary growth factors and proteins are shown in Table 10 below.

TABLE 10

Exemplary growth factors and proteins

| Exemplary Growth Factors and Proteins | Species | Accession No. |
|---|---|---|
| FGF-2 | Gallus gallus | P48800 |
| FGF-2 | Homo sapiens | P09038 |
| FGF-2 | Bos Taurus | P03969 |
| FGF-2 | Sus Scrofa | A0A287BGK8 |
| Ovotransferrin precursor | Gallus gallus | NP_990635 |
| Serotransferrin precursor | Bos taurus | NP_803450 |
| Serotransferrin isoform 1 precursor | Homo sapiens | NP_001054 |
| Serotransferrin | Ovis aries | XP_027816111 |
| Serotransferrin precursor | Mus musculus | NP_598738 |
| Serotransferrin precursor | Rattus norvegicus | NP_001013128 |
| Serotransferrin precursor | Sus scrofa | NP_001231582 |
| IGF1 isoform 1 preprotein | Homo sapiens | NP_001104753 |
| IGF1 preprotein | Gallus gallus | NP_001004384 |
| IGF1 precursor | Sus scrofa | NP_999421 |
| IGF1 precursor | Ovis aries | NP_001009774 |
| IGF1 isoform a preprotein | Rattus norvegicus | NP_001075946 |
| IGF 1 isoform 1 | Mus musculus | NP_034642 |
| IGF1 preprotein bovine | Bos Taurus | NP_001071296 |
| PDGF subunit B isoform 1 preprotein | Homo sapiens | NP_002599 |
| PDGF subunit B precursor | Gallus gallus | NP_989601 |
| PDGF subunit B precursor | Rattus norvegicus | NP_113712 |
| PDGF subunit B precursor | Mus musculus | NP_035187 |
| PDGF subunit B precursor | Bos taurus | NP_001017953 |
| Myogenic factor 6 (MYF6) | Homo sapiens | NM_002469 |
| Interleukin-6 precursor | Bos Taurus | NP_776348 |
| Interleukin 6 | Sus scrofa | CAM58482 |
| Interleukin 6 | Gallus gallus | ADL14564 |
| Interleukin-2 | Bos Taurus | ABK41607 |
| Interleukin-2 isoform X1 | Sus scrofa | XP_020956095 |
| Interleukin 2 | Gallus gallus | AAV35056 |
| Interleukin-3 | Bos Taurus | AAA99502 |
| Interleukin-3 | Gallus gallus | CAF18429 |
| Wnt-11 | Bos Taurus | XP_868944 |
| Wnt-11 | Sus scrofa | XP_020918191 |
| Wnt-11 | Gallus gallus | BAA06699 |
| Wnt-1 | Bos indicus x Bos taurus | XP_027399431 |
| Wnt-1 | Sus scrofa | XP_003126148 |
| Wnt-1 | Gallus gallus | XP_015128668 |
| Leukemia Inhibitory Factor | Bos Taurus | BAA19511 |
| Leukemia Inhibitory Factor | Sus scrofa | CAC14463 |
| Leukemia Inhibitory Factor isoform X1 | Gallus gallus | XP_425293 |

In some embodiments the cell culture media comprises Long arginine 3-IGF-1 (LR3-IGF1). The LR3 peptide chain provides higher stability to the protein. In some embodiments a Gallus gallus LR3-IGF1 comprises the amino acid sequence set forth in SEQ ID NO: 1 or a sequence having at least about 50%, at least about 60%, at least about 70%, at least about 80%, at least about 90%, at least about 95%, at least about 96%, at least about 97%, at least about 98%, at least about 99% sequence identity thereto. Exemplary LR3-IGF1 proteins are shown in Table 11 below.

TABLE 11

LR3-IGF1 sequences

| SEQ ID No. | LR3-IGF1 | Protein Sequence |
|---|---|---|
| 1 | Gallus gallus | MFPAMPLSSLFVNGPRTLCGAELVDALQFVCGDRGFYFSKPTGYG SSSRRLHHKGIVDECCFQSCDLRRLEMYCAPIKPPKSA |
| 2 | Homo sapiens | MFPAMPLSSLFVNGPRTLCGAELVDALQFVCGDRGFYFNKPTGYG SSSRRAPQTGIVDECCFRSCDLRRLEMYCAPLKPAKSA |

In some embodiments the cell culture media comprise one or more growth factors in the concentration range shown in Table 12 below.

TABLE 12

Exemplary growth factors and proteins

| Exemplary Growth Factors | Lowest Concentration (g/L) | Highest Concentration (g/L) |
|---|---|---|
| Insulin | 8.00E−04 | 0.008 |
| LR3-IGF1 | 0.009 | 0.04 |
| Transferrin (Holo) | 0.01 | 0.5 |
| FGF-2 | 1.00E−06 | 1.00E−03 |
| FGF-1 | 1.00E−06 | 1.00E−03 |
| PDGF | 1.00E−06 | 1.00E−03 |
| CTGF | 1.00E−06 | 1.00E−03 |
| EGF | 1.00E−06 | 1.00E−03 |
| TGFB | 1.00E−06 | 1.00E−03 |
| BMP | 1.00E−06 | 1.00E−03 |
| HGF | 1.00E−06 | 1.00E−03 |
| KGF | 1.00E−06 | 1.00E−03 |

Species-Specific Growth Factors Provided in Cis

In some embodiments, it may be desirable for cell-based meat of a particular genus/species to be cultured with cell media comprising growth factors derived from the same genus/species. Currently, only mouse and human-origin growth factors are widely available commercially and could be unfavorable or incompatible for growing agriculturally or nutritionally important animal cell lines, such as, but not limited to, chicken, beef, livestock, poultry, avian, game, or aquatic species. The unavailability, especially at industrial scale, of cell culture media for growing cell-based meat comprising high-fidelity species-matched growth factors is a challenge.

The present disclosure addresses this challenge by providing cell culture media comprising growth factors that match, or are cis, to the genus and/or species of the cell-based meat being cultured. As used herein, a cis growth factor is one that matches the genus and/or species of the cells in culture. This allows the cell culture medium to be customized to the cell-based meat being cultured, by using only species and/or genus-matched cells and growth factors. For instance, in such cis embodiments of the disclosure, if the cell culture medium is used to culture Gallus cells, the corresponding cis growth factors used in the cell media would be of Gallus origin, such as FGF-2 from Gallus gallus. The cis growth factor may comprise a sequence that is either naturally occurring, such as a wild-type sequence or a spontaneous mutation, or may comprise a sequence that is non-naturally occurring. For example, a cis growth factor comprising a non-naturally occurring sequence may be an engineered-variant of a naturally existing sequence. It is noted that, a cis growth factor comprising a non-naturally occurring sequence may not resemble the naturally occurring counterpart with much sequence similarity but retain similar function. The cis growth factors may be produced by a variety of methods known in the art, for example the growth factor may be recombinantly produced, isolated and purified or chemically synthesized. The cis growth factors of the present disclosure encompass naturally occurring homologs, paralogs and orthologs. Any growth factor may be provided in cis; exemplary growth factors that may be used as cis growth factors are shown in Table 10 above. In some embodiments the cis growth factor is a recombinant cis growth factor.

In some embodiments the variant cis growth factor is cis Gallus LR3-IGF1 (SEQ ID NO: 1, Table 11); the appended LR3 peptide chain provides higher stability to the protein.

Figure 3:
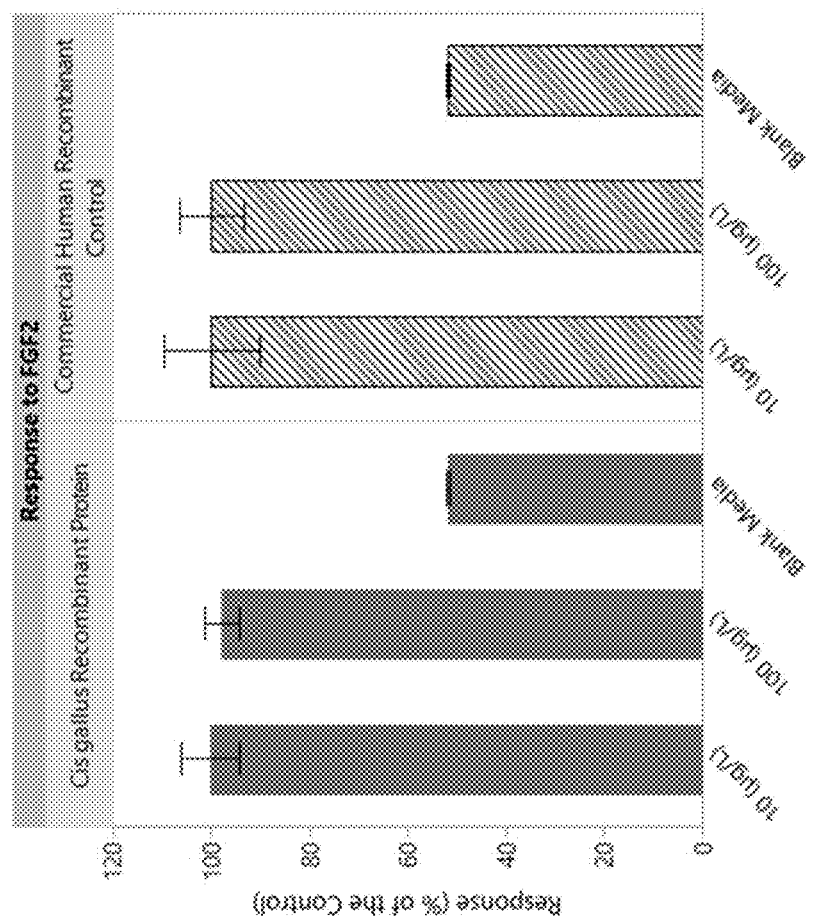
FIG. 3 shows a comparison of the response of *Gallus* cells cultured with cis *Gallus* recombinant FGF-2 vs. response with a commercial human recombinant FGF-2.

The use of cis growth factors is one of the many advantages of the cell culture media compositions of the present disclosure. Growth factors derived from agriculturally or nutritionally-relevant animal sources, such as chicken FGF or bovine IGF, are currently unavailable, especially at the industrial scale required for formulating cell culture media for growing cell-based meat economically. Cis recombinant growth factors may be produced as shown in Example 5 below. FIG. 3, and as detailed in Example 6, shows the cellular response of Gallus cells grown with either cis recombinant Gallus FGF-2, or commercially available human recombinant FGF-2 at different concentrations. An equivalent response was observed with both growth factors, showing no loss in activity upon using the cis recombinant Gallus FGF-2.

Figure 4:
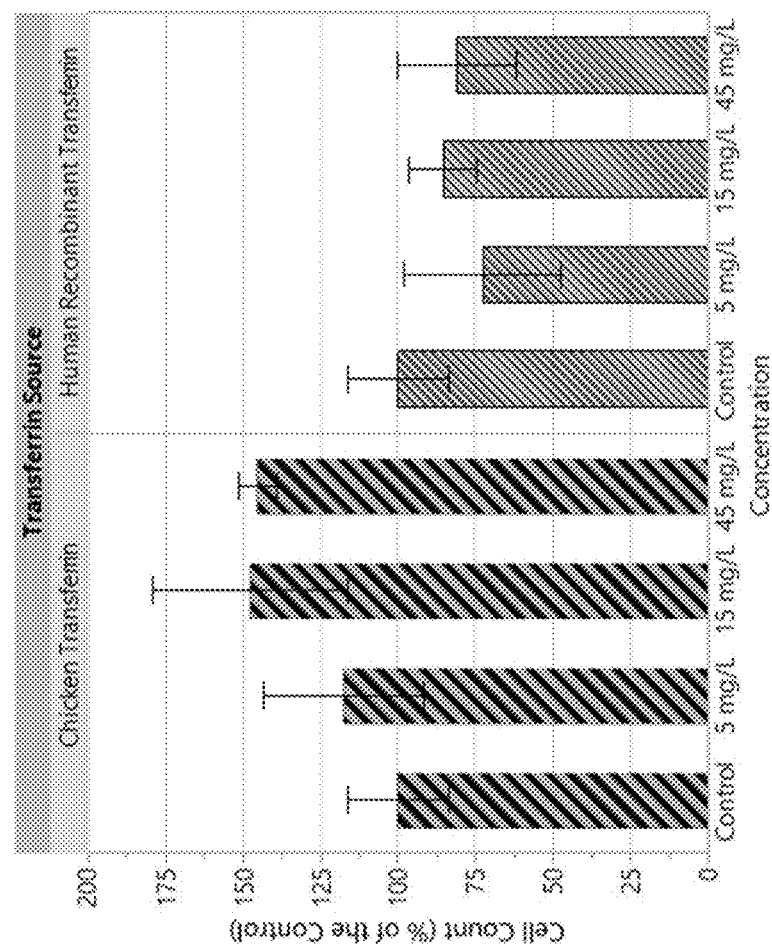
FIG. 4 shows a comparison of the growth of *Gallus* cells in adherent cultures, cultured with a medium comprising cis *Gallus* transferrin vs. growth in a medium comprising human recombinant transferrin.

In some embodiments the use of a cis growth factor provides enhanced cellular response, growth, efficacy, and/or activity compared to when using a non-cis growth factor. For example, culturing of cell-based meat in media comprising a cis growth factor may result in an increased growth rate of the cells compared to media comprising non-cis growth factors. As shown in FIG. 4 and detailed in Example 7, adherent Gallus cells grown in a medium comprising cis Gallus (chicken) transferrin showed higher cell growth compared to medium comprising human recombinant transferrin. The increased growth trend was observed at all three concentrations of cis Gallus transferrin and human recombinant transferrin tested. This demonstrates the ability of cell media comprising cis growth factors to outperform media with non-cis growth factors for production of cell-based meat.

Universal Growth Factors

The present disclosure provides novel growth factors that support the growth of cell-based meat of a plurality of genus and/or species and referred to herein as universal growth factors. In some embodiments, the universal growth factors support the growth of cell-based meat of any genus and/or species. By way of a non-limiting example, a universal FGF-2, universal PDGF-BB, universal IGF-1, or universal VEGF-A may be used in a cell culture medium to grow cell-based chicken, beef, livestock, poultry, avian, game, or aquatic species. Cell media containing universal growth factors provide multiple advantages, such as applicability independent of the cells being cultured, off-the-shelf availability, and reduced costs.

In some embodiments the universal growth factor is selected from the group consisting of universal FGF-2 (SEQ ID NO: 3), universal PDGF-BB (SEQ ID NO: 5), universal IGF-1 (SEQ ID NO: 6), and universal VEGF-A (SEQ ID NO: 7) or a sequence having at least about 50%, at least about 60%, at least about 70%, at least about 80%, at least about 90%, at least about 95%, at least about 96%, at least about 97%, at least about 98%, at least about 99% sequence identity thereto.

In some embodiments, the universal growth factor may be universal across kingdom, phylum, class, order, family, genus and/or species. In some embodiments, the universal growth factor may be universal across the metazoan division of the animal kingdom.

In some embodiments, the universal growth factor is universal only across certain kingdom, phylum, class, order, family, genus and/or species. For example, a universal growth factor may be universal across any one of mammals, birds, fish, reptiles, amphibians, and arthropods. In some embodiments a universal mammalian growth factor may be used across the board to culture mammalian cell-based meat.

The universal growth factors of the disclosure may be recombinantly produced, isolated/purified, and/or chemically synthesized. In some embodiments, universal growth factors are designed in silico and produced recombinantly as described in Example 4. Exemplary recombinant universal growth factors are shown in Table 13.

Adhesion Proteins

In some embodiments the cell culture media comprise one or more adhesion proteins. Examples of adhesion proteins include collagen, collagen IV alpha 1, fibronectin, TPA: Fibronectin, partial Fibronectin vitronectin, fibrinogen variants, precursors, isoforms, homologs, paralogs, orthologs, and biologically active fragments thereof. Exemplary adhesion proteins are shown in Table 14 below.

TABLE 14

Exemplary adhesion proteins

| Exemplary Adhesion Proteins | Species | Accession No. |
| --- | --- | --- |
| Vitronectin | Bos Taurus | AAI03133 |
| Vitronectin | Sus scrofa | BAA09616 |
| Vitronectin | Gallus Gallus | CAA71914 |
| Collagen alpha-3(IV) | Bos Taurus | Q28084 |
| Collagen, type IV, alpha 1 | Sus scrofa | JAA74162 |
| Collagen type VI subunit alpha-1, partial | Gallus Gallus | CAA41053 |
| TPA: fibronectin | Bos Taurus | DAA32456 |
| Fibronectin, partial | Sus scrofa | AAW02948 |
| Fibronectin | Gallus Gallus | P11722 |

Other Cis and Universal Media Components

In some embodiments any protein included in the cell media of the disclosure may be used provided in cis. For instance, when culturing *Gallus* cells, the adhesion protein fibronectin used may be a *Gallus* fibronectin. The cis adhesion protein may be recombinantly produced, isolated/purified, or chemically synthesized.

TABLE 13

Exemplary recombinant universal growth factors

| Seq ID No. | Exemplary Recombinant Universal Growth Factors | Sequences |
| --- | --- | --- |
| 3 | universal FGF-2 | MAAGSITTLPALPEDGGSGAFPPGHFKDPKRLYCKNGGFFLRIHPDGRV DGVREKSDPHIKLQLQAEERGVVSIKGVCANRYLAMKEDGRLLASKCV TDECFFFERLESNNYNTYRSRKYSSWYVALKRTGQYKLGSKTGPGQKA ILFLPMSAKS |
| 4 | universal FGF-2 | ATG GCA GCA GGT AGT ATT ACT ACG CTT CCC GCC CTT CCC GAA GAC GGG GGT TCA GGT GCC TTC CCG CCG GGG CAT TTT AAA GACCCG AAG CGC CTT TAC TGT AAG AAT GGG GGC TTT TTC TTG CGT ATC CAC CCA G?C GGC CGC GTG G?C GGT GTG CGT GAA AAA TCCGAT CCA CAT ATT AAA CTT CAG CTT CAA GCA GAA GAG CGT GGT GTG GTT TCC ATC AAG GGG GTG TGT GCC AAC CGC TAT CTT GCGATG AAG GAG GAC GGT CGT CTG CTG GCT TCG AAA TGT GTT ACC GAC GAG TGT TTT TTC TTC GAG CGC CTG GAA TCA AAT AAT TACAAC ACC TAC CGC AGC CGC AAA TAT TCT TCA TGG TAC GTG GCT TTG AAG CGC ACA GGT CAG TAT AAA TTG GGC AGT AAA ACG GGTCCA GGA CAG AAG GCG ATT CTT TTC TTA CCG ATG TCA GCT AAA AGC TAA TGA |
| 5 | universal PDGF-BB | SLGSLAAAEPAVIAECKTRTEVFEISRRLIDRTNANFLVWPPCVEVQRCS GCCNNRNVQCRPTQVQDRPVQVRKIEIVRKKPIFKKATVTLEDHLACKC ETVVARAVT |
| 6 | universal IGF-1 | MGKISSLPTQLFKCCFCDFLKVKMHVTSSSHLFYLALCLLTFTSSATAGP ETLCGAELVDALQFVCGDRGFYFNKPTGYGSSSRRAPQTGIVDECCFRS CDLRRLEMYCAPLKPAKSARSVRAQRHTDMPKAQKEVHLKNTSRGSA GNKNYRM |
| 7 | universal VEGF-A | MNFLLSWVHWSLALLLYLHHAKWSQAAPMAEGGQKPHEVVKFMDVY QRSFCRPIETLVDIFQEYPDEIEFIFKPSCVPLMRCGGCCNDEsLECVPTEE fNITMQIMRIKPHQsQHIGEMSFLQHNKCECRPKKDKARQENPCGPCSER RKHLFVQDPQTCKCSCKNTDSRCKARQLELNERTCRCdkpRR |

In some embodiments any protein included in the cell media of the disclosure may be universal. For instance, the adhesion protein fibronectin may be used to develop a universal fibronectin by methods described in the present disclosure.

Methods for Formulating a Cell Culture Medium

Provided herein are methods of formulating the cell culture medium (nutrient medium) of the present disclosure, useful for culturing slaughter-free meat.

In some embodiments provided herein is a method for formulating a nutrient medium for the production of slaughter-free meat comprising: (a) providing a plurality of ingredients; and (b) one or more of: (i) replacing one or more ingredients currently not approved for use in food with an ingredient approved for use in food; (ii) removing one or more ingredients currently not approved for use in food; and (iii) formulating one or more ingredients currently not approved for use in food at or below ADI value. In some embodiments the cell culture medium produced by the method is chemically defined.

Methods for formulating the cell culture media of the present disclosure for production of cell-based meat is a highly challenging and unpredictable process. Unlike conventional cell culture media (e.g. Ham's F-12, DMEM, Medium 199) used in pharmaceutical and biotechnological applications, several challenges were overcome in the development of safe and effective cell culture media of the present disclosure for production of cell-based meat. The cell culture media of the present disclosure were developed by balancing safety on one hand, while maintaining, if not exceeding, the media performance for culturing cells and tissues. Replacement, removal and/or reduction of ingredients to confer edibility on the media in most instances led to a drop in performance of the cell culture medium, for example as assessed by cell viability and cell growth. After much experimentation and novel approaches, cell media compositions and methods for formulating the cell culture media were identified. Specific examples of replacing, removing, and/or reducing media ingredients below ADI values are discussed below without compromising performance. Further, an exemplary safety assessment framework and a 3-tier categorization system is detailed below, along with specific examples of ingredients in Table 16.

Figure 5:
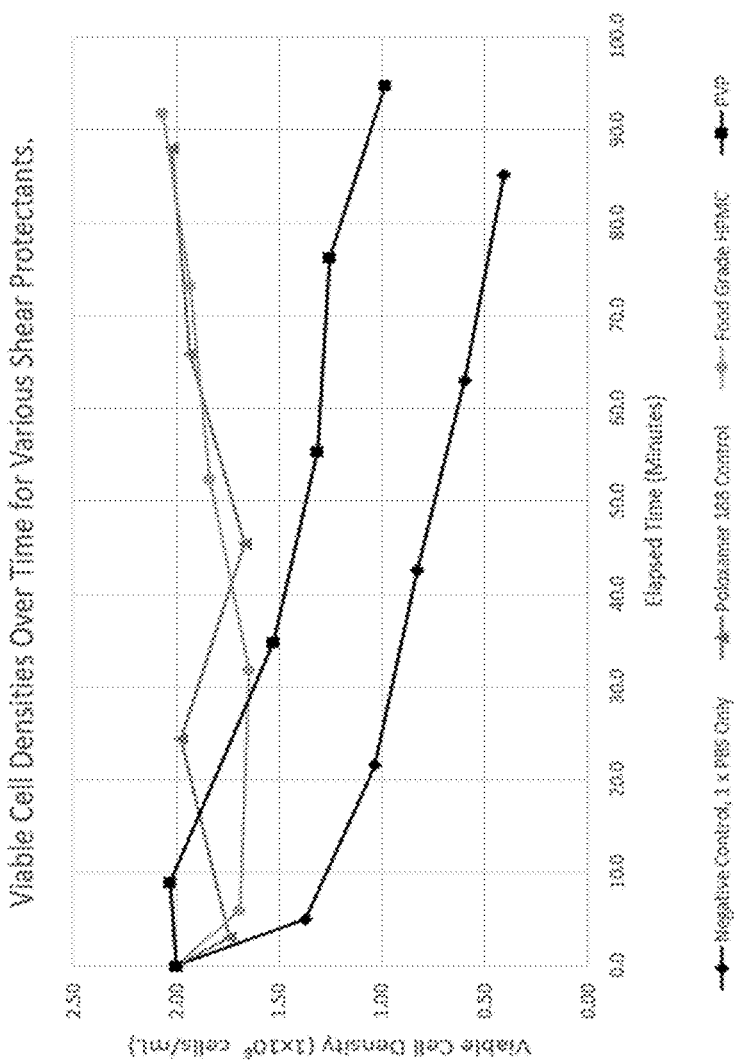
FIG. 5 shows a comparison of cell viability over time for various shear protectants.

By way of example, poloxamers, such as Poloxamer 188, are surfactants used in cell culture bioprocesses as shear protectants, and thus are commonly provided in conventional cell culture media. Poloxamers are not approved for use in food. To find a suitable food-safe replacement, several compounds with GRAS approval notifications and potential shear protectant properties were identified and screened, such as polyvinyl alcohol (PVA), polyvinylpyrrolidone (PVP), and several versions of methylcellulose. As shown in FIG. 5, the performance indicator, cellular viability, was monitored over time in the presence of various shear protectants. In the absence of a shear protectant (negative control), the cell viability rapidly declined over time. In the presence of PVP, a similar decline was noted while poloxamer 188 maintained viability as expected. Unexpectedly, hydroxypropyl methylcellulose (HPMC) was found to offer sufficient shear protection to maintain cell viability after the removal of poloxamer 188. However, effective shear protection alone is not enough for determining a replacement to poloxamer. Other critical properties, such as solubility, particle size, temperature effects also had to be tested. HPMC was found to be sufficiently soluble as well as filterable, whereas many other food-safe shear protectants failed. Given the vastly different chemical structures and physico-chemical characteristics of poloxamer, PVA, PVP and HPMC, it is not possible to predict required properties, such as shear protection and solubility to name a few. A variety of conditions were tested to arrive at the present cell media compositions of the present disclosure, such as HPMC described above. In some embodiments the method comprises removing poloxamer. In some embodiments the method comprises replacing poloxamer with methylcellulose. In some embodiments the method comprises replacing poloxamer with hydroxypropyl methylcellulose. In some embodiments the method comprises reducing the formulation of poloxamer in the cell culture medium to or below its ADI value.

Cobalt is an essential cofactor nutrient for many enzymatic pathways that contribute to metabolic and cellular function. Cobalt chloride is a commonly used source of cobalt in culture media. Cobalt chloride is strictly prohibited by the FDA for use in food. In order to find a suitable replacement, many cobalt compounds were screened. Eventually, Vitamin B12 in the form of cyanocobalamin, which contains bioavailable cobalt at its chiral center, was found. The replacement of cobalt chloride with cyanocobalamin sufficiently supplied cobalt as a food-safe cofactor to promote cellular function. In some embodiments the method comprises removing cobalt chloride. In some embodiments the method comprises replacing cobalt chloride with cyanocobalamin (Vit B12).

Figure 6:
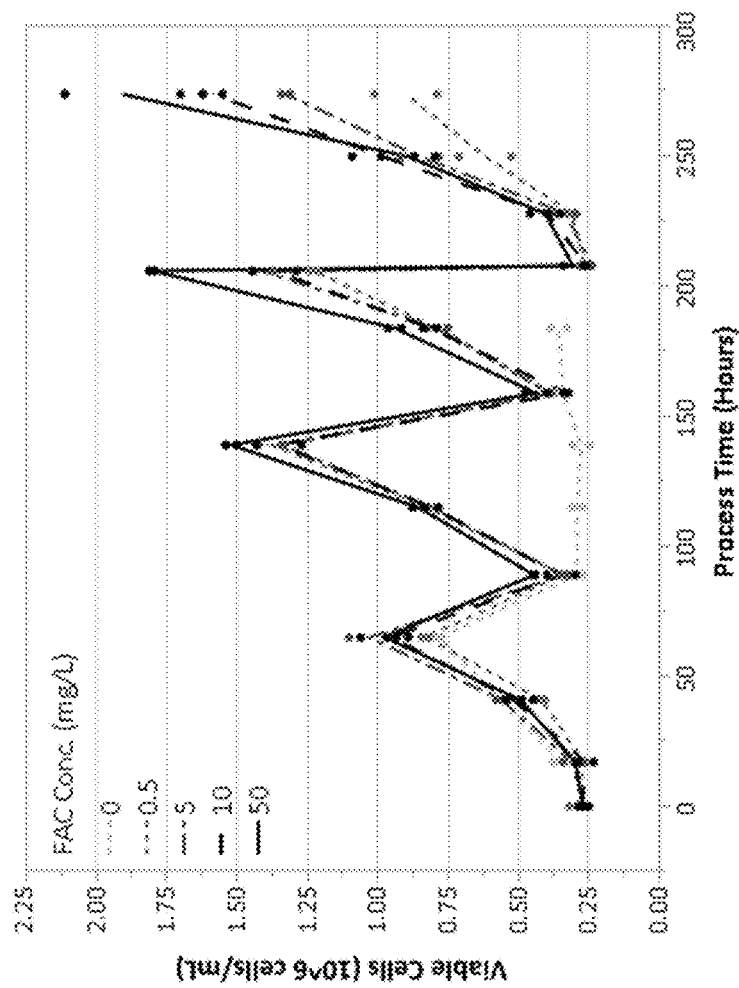
FIG. 6 shows cell viability over time in the absence and presence of ferric ammonium citrate at different concentrations.

Several trace elements are essential to cell metabolism and growth. Such elements may either be vastly reduced or removed completely from the media formulation in order to meet safety standards. Table 15 shows several different components that were either adjusted to be at levels below the ADI level or that were removed completely from the media formulation. As a novel alternative to formulating trace elements directly, the present disclosure discloses the identification and testing of food-safe complexes that innately contain trace elements. For example, ferric ammonium citrate (FAC) is a complex of ammonia, citrate and iron that is commonly used as a food additive/ingredient. FAC is known to have small amounts of many trace element nutrients due to the process by which it is harvested and produced. Cell studies showed that by adding FAC into the media of the present disclosure, the cells were supplied with the trace amounts of these minerals required for robust cell growth. As shown in FIG. 6, cells supplemented with FAC at various concentrations (0.5 mg/ml-50 mg/ml) maintain high viability over time (up to 275 hours) compared to cells without FAC supplementation. Thus, cells supplemented with FAC did not exhibit a drop in performance after the components in Table 14 were reduced/removed.

TABLE 15

Exemplary trace elements and other components

| Name | CAS# | ADI (mg/kg bw-day) |
|---|---|---|
| RUBIDIUM CHLORIDE | 7791-11-9 | 0.051 |
| STRONTIUM CHLORIDE HEXAHYDRATE | 10025-70-4 | 1.87 |
| SODIUM METAVANADATE | 13718-26-8 | 0.274 |
| SODIUM MOLYBDATE-2H$_2$O | 10102-40-6 | 1.41 |
| HYPOXANTHINE-NA | 45738-97-4 | 0.3 |

TABLE 15-continued

Exemplary trace elements and other components

| Name | CAS# | ADI (mg/kg bw-day) |
|---|---|---|
| PUTRESCINE-2HCl | 333-93-7 | 0.018 |
| THYMIDINE SYNTHETIC | 50-89-5 | 83.1 |
| DL-ALPHA-LIPOIC ACID | 1077-28-7 | 5.14 |

In some embodiments the method comprises removing one or more of ammonium molybdate, sodium molybdate, ammonium metavanadate, sodium metavanadate, rubidium chloride, strontium chloride hexahydrate, hypoxanthine, putrescine, thymidine, and DL-alpha lipoic acid. In other embodiments the method comprises replacing one or more of ammonium molybdate, sodium molybdate, ammonium metavanadate, sodium metavanadate, rubidium chloride, and strontium chloride hexahydrate with ferric ammonium citrate. In other embodiments the method comprises replacing one or more of hypoxanthine, putrescine, and thymidine with optimized amino acid blends within the concentration ranges shown in Table 1. In other embodiments the method comprises replacing DL-alpha lipoic acid with plant derived oils or yeast hydrolysates. In some embodiments the method comprises reducing formulation of one or more of ammonium molybdate, sodium molybdate, ammonium metavanadate, sodium metavanadate, rubidium chloride, strontium chloride hexahydrate, hypoxanthine, putrescine, thymidine, and DL-alpha lipoic acid to or below their respective ADI values.

In some embodiments the method comprises removing an anti-foaming agent currently not approved for use in food. In some embodiments the method comprises replacing the anti-foaming agent currently not approved for use in food with simethicone. In some embodiments the method comprises reducing the formulation of the anti-foaming agent currently not approved for use in food in the cell culture medium to or below its ADI value.

In some embodiments the cell culture medium produced by the method contains no more than 10%, 9%, 8%, 7%, 6%, 5%, 4%, 3%, 2%, 1%, 0.5%, 0.1% or no more than 0.01%% animal-derived serum. In some embodiments the cell culture medium produced by the method is substantially free of animal-derived serum or free of animal-derived serum.

In some embodiments the cell culture medium produced by the method is does not comprise any components associated with blood.

In some embodiments the cell culture medium produced by the method contains no more than 10%, 9%, 8%, 7%, 6%, 5%, 4%, 3%, 2%, 1%, 0.5%, 0.1% or no more than 0.01%% animal-derived components. In some embodiments the cell culture medium produced by the method is substantially free of animal-derived components or free of animal-derived components.

In some embodiments the cell culture medium produced by the method may be used in batch, fed-batch, chemostat, perfusion, and/or intensified bioreactor tissue cultivator processes.

In some embodiments the cell culture medium produced by the method comprises any one or more of growth factors, universal growth factors, and/or cis growth factors described in the present disclosure. In some embodiments the cell culture medium produced by the method comprises any one or more of the growth factors set forth in SEQ ID NOs: 1-7. In some embodiments the cell culture medium produced by the method comprises any one or more of the ingredients described in the present disclosure.

The present disclosure also provides a safety assessment framework for evaluating the use of media formulations in cell-based meat production, and for safety evaluation. A safety assessment was conducted on each component of a given cell culture media under the procedure outlined below. Most media components are nutrients and have existing regulatory status for various specified food uses; therefore, the evaluation begins with a consideration of the regulatory status of each compound. Further overview of the categorical framework for ensuring that culture media components are safe and suitable for their intended use in meat production are outlined below according to their category designation. A list of media components used during meat production along with worst-case exposure estimates and relevant authoritative limits or published toxicological/safety data supporting their use is presented in Table 16.

Category 1: These cell culture media components are food ingredients/additives that are GRAS or permitted by federal regulation without limitation on use. Exemplary compounds in this category include innocuous ingredients such as sugars, pH buffers, water soluble vitamins, and common antioxidants such as tocopherols.

Category 2. These cell culture media components are common dietary nutrients and are anticipated to have GRAS status for food use or be permitted by regulation for addition to food. Examples of such compounds include most of the inorganic salts and macronutrients that are present within the cell culture media. Where these compounds are permitted for direct addition to food at use levels comparable to anticipated concentrations that might reasonably be expected in the cell-based meat product, no safety concerns are anticipated. Majority of nutrients present within the poultry cell-based meat may be readily measured using common validated methods for food composition testing. Batch analyses of multiple lots of the finished product may be obtained to validate the above assumptions. In some instances, consideration of established safe levels (e.g., ADI, UL) derived from a relevant authoritative body (e.g., U.S. FDA, EFSA, JECFA, FSANZ, U.S. EPA) may be leveraged to support safety. If comparisons of anticipated dietary intakes relative to an authoritative reference intake value is used, consideration of additive intakes from all dietary sources may be considered. In the absence of an authoritative reference intake value, published NOAELs from animal toxicology studies may be used to evaluate safety using standard scientific procedures for food safety evaluation. A margin of exposure (MoE) of 100-fold or greater between the NOAEL and estimated dietary intakes from food exposures is typically considered adequate to support safety. In situations where the MoE is <100-fold, additional measures for further reduction of the media component may be necessary, or further characterization of intraspecies/interspecies differences in metabolism may be necessary. These situations also require careful consideration of the regulatory status on a case-by-case basis (e.g., premarket approval as a food additive or GRAS evaluation required).

Category 3. These cell culture media components have not been previously used in food production (e.g., no federal regulations or previous GRAS status) but with sufficient information to conclude that the compounds do not present risk for intended use in food production. For example, situations where the compound is not detectable in finished product or is present at equivalent levels in comparator foods, compounds that are thermo-labile and will be digested during cooking, and/or compounds that are expected to be digested to innocuous compounds following ingestion. Examples of compounds meeting the aforementioned conditions would include recombinant growth factors and serum components. For Category 3 substances a final consideration in the safety assessment process may involve hazard characterization of the potential for a substance to produce toxic biological effects outside of the endpoints measured in a sub-chronic rat toxicity study. Substances with biological activity may require additional hazard characterization related to reproductive and developmental toxicity, or immunotoxicity. Considerations for allergenicity, biological effects in humans (e.g., effects on blood pressure), and synergistic effects with other media components also may be evaluated. Such investigations may preferably be evidence-based (i.e., availability of a clinical trial demonstrating that a substance affects blood pressure), rather than theoretical (i.e., based on presumptive mechanisms of action). Similar to category 2 substances, the regulatory status of ingredients in category 3 will require case-by-case evaluation of the regulatory status of the compound (e.g., need for premarket approval or GRAS evaluation). Examples of category 3 components include recombinant proteins and animal serum.

TABLE 16

Exemplary List of Cell Culture Media Ingredients Used During Meat Production, Risk Categorization, and Safety Information

| Class | Compound | CAS # | Risk Assessment Category | Maximum Estimated Exposure per 100 g serving** | Safe Reference Level for Human Dietary Intake (e.g., UL, OSL) |
|---|---|---|---|---|---|
| Amino Acids | L-ALANINE | 56-41-7 | 2 | N/A* | UL = N/A* |
| | L-ARGININE-HCL | 1119-34-2 | 2 | N/A* | UL = N/A* |
| | L-ASPARAGINE-H20 | 5794-13-8 | 2 | N/A* | UL = N/A* |
| | L-ASPARTIC ACID | 56-84-8 | 2 | N/A* | UL = N/A* |
| | L-CYSTEINE HCL H20 | 7048-04-06 | 2 | N/A* | UL = N/A* |
| | L-CYSTINE 2HCL | 56-89-3 | 2 | N/A* | UL = N/A* |
| | L-GLUTAMIC ACID MONOSODIUM H20 | 6106-04-03 | 2 | N/A* | UL = N/A* |
| | L-GLUTAMINE | 56-85-9 | 2 | N/A* | UL = N/A* |
| | GLYCINE | 56-40-6 | 2 | N/A* | UL = N/A* |
| | L-HISTIDINE-HCL-H20 | 5934-29-2 | 2 | N/A* | UL = N/A* |
| | L-ISOLEUCINE | 73-32-5 | 2 | N/A* | UL = N/A* |
| | L-LEUCINE | 61-90-5 | 2 | N/A* | UL = N/A* |
| | L-LYSINE-HCL | 657-27-2 | 2 | N/A* | UL = N/A* |
| | L-METHIONINE | 63-68-3 | 2 | N/A* | UL = N/A* |
| | L-PHENYLALANINE | 63-91-2 | 2 | N/A* | UL = N/A* |
| | L-PROLINE | 147-85-3 | 2 | N/A* | UL = N/A* |
| | L-SERINE | 56-45-1 | 2 | N/A* | UL = N/A* |
| | L-THREONINE | 72-19-5 | 2 | N/A* | UL = N/A* |
| | L-TRYPTOPHAN | 73-22-3 | 2 | N/A* | UL = N/A* |
| | L-TYROSINE-2NA-2H20 | 122666-87-9 | 2 | N/A* | UL = N/A* |
| | L-VALINE | 72-18-4 | 2 | N/A* | UL = N/A* |
| Carbon substrates | D-GLUCOSE | 50-99-7 | 1 | N/A | NS |
| | SUCCINIC ACID | 110-15-6 | 2 | 200 mg | Intakes for a 65 kg adult are 257-fold below NOAEL from 2 year rat study |
| | SODIUM SUCCINATE-2Na 6H20 | 6106-21-4 | 2 | 40 mg | Intakes for 65 kg adults are >1000 fold below NOAEL from 2 year rat study. |
| | SODIUM PYRUVATE | 113-24-6 | 3 | 1 g | Dietary intakes within the range of OSL valued reported in human investigations |
| Vitamins | FOLIC ACID | 59-30-3 | 1 | 60 mg | UL = 300 to 1000 ug/d (upper limit not established based on toxicity, but to prevent people who don't know they have a vitamin B deficiency from consuming too much folic acid) |
| | DL-ALPHA-TOCOPHEROL ACETATE | 7695-91-2 | 1 | 8 mg | UL = 1000 mg/d |
| | VITAMIN D2 (ERGOCALCIFEROL) | 50-14-6 | 1 | 24 ug | UL = 100 ug/d |

TABLE 16-continued

Exemplary List of Cell Culture Media Ingredients Used
During Meat Production, Risk Categorization, and Safety Information

| Class | Compound | CAS # | Risk Assessment Category | Maximum Estimated Exposure per 100 g serving** | Safe Reference Level for Human Dietary Intake (e.g., UL, OSL) |
|---|---|---|---|---|---|
| | D-ALPHA-TOCOPHEROL | 59-02-9 | 1 | 1.6 mg | UL = 1000 mg/d |
| | D-BIOTIN | 58-85-5 | 1 | 4 mg | UL = N/A |
| | MYO-INOSITOL | 87-89-8 | 1 | 430 mg | OSL = 4 g/d |
| | NIACINAMIDE (NICOTINAMIDE) | 98-92-0 | 1 | 25 mg | UL = 10 to 35 mg (supplements) |
| | PYRIDOXINE-HCL | 58-56-0 | 1 | 25 mg | UL = 30 to 100 mg |
| | PYRIDOXAL-HCL | | 1 | | UL = 30 to 100 mg |
| | RIBOFLAVIN | 83-88-5 | 1 | 3.7 mg | UL = NS |
| | THIAMINE-HCL | 67-03-8 | 1 | 18 mg | UL = NS |
| | VITAMIN B12 (CYANCOCOBALAMIN) | 68-19-9 | 1 | 2 mg | UL = NS |
| | CALCIUM D-PANTOTHENATE | 0137-08-06 | 1 | 100 mg | UL = NS |
| | CHOLINE CHLORIDE | 67-48-1 | 1 | 52 mg | UL = 3.5 g/d |
| | ASCORBIC ACID | | 1 | 2 g | UL = 400 to 2000 mg (theoretical ascorbic acid concentrations represent gross over estimates and likely exceed concentrations by an order of magnitude and are expected to be present at levels well below the UL). |
| Trace Metals | SODIUM CHLORIDE | 7647-14-5 | 1 | — | 2.3 g/d |
| | CALCIUM CHLORIDE (ANHY) | | 1 | 760 mg | 1 to 3 g/d |
| | MANGANESE SULFATE H20 | 10034-96-5 | 1 | 3 ug | 2 to 11 mg/d |
| | POTASSIUM CHLORIDE | 7447-40-7 | 1 | 4 g | UL = NS |
| | MAGNESIUM CHLORIDE (ANHY) | | 1 | 170 mg | 65 to 350 mg |
| | COPPER SULFATE-PENTAHYDRATE | 7758-99-8 | 1 | 3 mg | 1 to 10 mg |
| | SODIUM METASILICATE-9H2O | 13517-24-3 | 1 | 1.6 mg | Intakes for a 65 kg adult are 31,000 fold below rat NOAEL |
| | SODIUM SELENITE (ANHY) | 10102-18-8 | 2 | 190 ug | Intakes for 65 kg adult are 133-fold below 13 week rat NOAEL |
| | ZINC SULFATE-7H20 | 7446-20-0 | 1 | 15 mg | UL = 5 to 40 mg/day |
| | MAGNESIUM SULFATE (ANHY) | 7487-88-9 | 1 | 493 mg | No UL for food sources; UL = 65 to 350 mg (dietary supplements) |
| | FERRIC NITRATE-9H2O | 7782-61-8 | 3 | 0.3 mg | Iron UL = 40 to 45 mg; Nitrate ADI = 3.7 mg/kg bw/day (levels of iron and nitrate are orders of magnitude below the UL and ADI) |
| | FERROUS SULFATE-7H2O | 7782-63-0 | 2 | 2.5 mg | Iron UL = 40 to 45 mg |
| | FERRIC CITRATE | 3522-50-7 | 2 | (Present as a residue of seed-train scale-up and not used as nutrient source of iron) | Iron UL = 40 to 45 mg |
| | FERRIC AMMONIUM CITRATE | 1185-57-5 | 2 | (Present as a residue of seed-train scale-up and not used as nutrient source of iron) | Iron UL = 40 to 45 mg |
| Iron Carrier | Bovine Transferrin | 11096-37-0 | 3 | 150 mg | NR |
| | SODIUM PHOSPHATE MONOBASIC H20 | 10049-21-5 | 1 | 1.5 g | NR |
| | SODIUM | 7558-79-4 | 1 | 4.3 g | NR |

TABLE 16-continued

Exemplary List of Cell Culture Media Ingredients Used
During Meat Production, Risk Categorization, and Safety Information

| Class | Compound | CAS # | Risk Assessment Category | Maximum Estimated Exposure per 100 g serving** | Safe Reference Level for Human Dietary Intake (e.g., UL, OSL) |
|---|---|---|---|---|---|
| | PHOSPHATE DIBASIC-ANHY | | | | |
| Supplementary Lipids | LINOLEIC ACID | 60-33-3 | 2 | 1 mg | AI = 7 to 12 g/d |
| Emulsifier | MONOETHANOLAMINE | 141-43-5 | 2 | 160 mg | Dietary intakes for 65 kg adult are 128 fold below rat NOAEL |
| Surfactant/ Emulsifier | TWEEN 80 | 9005-65-6 | 2 | 4 mg | ADI = 10 mg/kg bw/d |
| Antioxidant | L-GLUTATHIONE | 70-18-8 | 2 | 36 mg | NR |
| Animal components | CHICKEN SERUM | www.thermofisher.com/us/en/home/life-science/cell-culture/mammalian-cell-culture/fbs/other-sera/chicken-serum.html | 3 | — | NR |
| | BOVINE SERUM | www.thermofisher.com/order/ catalog/product/16170060?SID=srch-srp-16170060#/16170060?SID=srch-srp-16170060 | 3 | — | NR |
| | BOVINE SERUM ALBUMIN | www.thermofisher.com/order/catalog/product/11020021#/11020021 | 3 | — | NR |
| Hydrolysate | HYPEP 2 YEAST EXTRACT | 8013-01-02 | 2 | 2 g | NR |
| Growth Factors | FGF2 (FIBROBLAST GROWTH FACTOR-BASIC) | N/A | 3 | — | NR |
| | PDGF-BB (PLATELET DERIVED GROWTH FACTOR-BB) | N/A | 3 | — | NR |
| | IGF-1 (INSULIN-LIKE GROWTH FACTOR 1) | N/A | 3 | — | NR |
| Peptides | RGD | 99896-85-2 | | 0.3 ug (Present as a residue of seed-train scale-up and is not directly added to meat production media) | N/A |
| | YIGSR | 110590-64-2 | | 0.3 ug (Present as a residue of seed-train scale-up, not directly added to meat production media) | |

AI = Adequate Intake
ADI = Acceptable Daily Intake
FNB-IOM = Food and Nutrition Board of the Institute of Medicine
HDT = Highest Dose Tested
N/A = Not applicable
NR = Not reported
NS = not specified as no evidence of toxicity from excess intake known
NOAEL = No Observed Adverse Effect Level
UL = Tolerable Upper Limit
OSL = Observed Safe Level
*No upper limit when provided as dietary protein
**Maximum dietary exposures estimated using conservative assumption of complete transfer of media components to the finished product on a wt/wt basis.

EXEMPLARY EMBODIMENTS

Embodiment I-1. A cell culture medium comprising a plurality of ingredients, wherein each ingredient is approved for use in food and/or is at or below its ADI value.

Embodiment I-2. The medium of embodiment I-1, wherein the medium is edible.

Embodiment I-3. The medium of embodiment I-1 or I-2, wherein the ingredient approved for use in food is Generally Recognized As Safe (GRAS).

Embodiment I-4. The medium as in one of embodiments I-1 to I-3, wherein the ingredient is approved for use in food by the FDA.

Embodiment I-5. The medium as in one of embodiments I-1 to I-4, wherein the ingredient is approved for use in food by the USDA.

Embodiment I-6. The medium as in one of embodiments I-1 to I-5, wherein the ingredient is approved for use in food by the *Codex alimentarius*.

Embodiment I-7. The medium as in one of embodiments I-1 to I-6, wherein the ingredient is approved for use in food by the European Food Safety Authority.

Embodiment I-8. The medium as in one of embodiments I-1 to I-7, wherein the ingredient is approved for use in food by the Food Chemicals *Codex*.

Embodiment I-9. The medium as in one of embodiments I-1 to I-8, wherein the medium contains no more than 10%, 9%, 8%, 7%, 6%, 5%, 4%, 3%, 2%, 1%, 0.5%, 0.1%, 0.05% or no more than 0.01%% animal-derived serum.

Embodiment I-10. The medium as in one of embodiments I-1 to I-9, wherein the medium is substantially free of animal-derived serum.

Embodiment I-11. The medium as in one of embodiments I-1 to I-10, wherein the medium is free of animal-derived serum.

Embodiment I-12. The medium as in one of embodiments I-1 to I-11, wherein the medium contains no more than 10%, 9%, 8%, 7%, 6%, 5%, 4%, 3%, 2%, 1%, 0.5%, 0.1%, 0.05% or no more than 0.01%% animal-derived components.

Embodiment I-13. The medium as in one of embodiments I-1 to I-12, wherein the medium is substantially free of animal-derived components.

Embodiment I-14. The medium as in one of embodiments I-1 to I-13, wherein the medium is free of animal-derived components.

Embodiment I-15. The medium as in one of embodiments I-1 to I-14, wherein the medium is chemically defined.

Embodiment I-16. The medium as in one of embodiments I-1 to I-15, further comprising a growth factor.

Embodiment I-17. The medium of embodiment I-16, wherein the growth factor is a universal growth factor.

Embodiment I-18. The medium of embodiment I-17, wherein the universal growth factor is FGF-2.

Embodiment I-19. The medium of embodiment I-18, wherein the FGF-2 comprises an amino acid sequence set forth in SEQ ID NO: 3.

Embodiment I-20. The medium of embodiment I-18, wherein the FGF-2 is encoded by a nucleic acid sequence set forth in SEQ ID NO: 4.

Embodiment I-21. The medium of embodiment I-17, wherein the universal growth factor is a PDGF-BB.

Embodiment I-22. The medium of embodiment I-21, wherein the PDGF-BB comprises an amino acid sequence set forth in SEQ ID NO: 5.

Embodiment I-23. The medium of embodiment I-17, wherein the universal growth factor is IGF-1.

Embodiment I-24. The medium of embodiment I-23, wherein the IGF-1 comprises an amino acid sequence set forth in SEQ ID NO: 6.

Embodiment I-25. The medium of embodiment I-17, wherein the universal growth factor is VEGF-A.

Embodiment I-26. The medium of embodiment I-25, wherein the VEGF-A comprises an amino acid sequence set forth in SEQ ID NO: 7.

Embodiment I-27. The medium of embodiment I-16, wherein the medium is used for culturing cell-based meat and the growth factor is a cis growth factor, wherein the cis growth factor matches the genus of the cells in culture.

Embodiment I-28. The medium of embodiment I-27, wherein the use of the cis growth factor allows for enhanced cell growth compared to a non-cis growth factor.

Embodiment I-29. The medium of embodiment I-28, where the cis growth factor is cis *Gallus* transferrin.

Embodiment I-30. The medium of embodiment I-27, wherein the cis growth factor is a variant of the corresponding naturally existing growth factor of the genus of the cells in culture.

Embodiment I-31. The medium of embodiment I-30, wherein the cis growth factor variant is *Gallus* LR3-IGF1.

Embodiment I-32. The medium of embodiment I-31, wherein the *Gallus* LR3-IGF1 comprises an amino acid sequence set forth in SEQ ID NO: 1.

Embodiment I-33. The medium of embodiment I-16, wherein the growth factor is selected from the group consisting of IGF-1, LR3-IGF1, FGF-1, FGF-2, PDGF, CTGF, EGF, TGFB, BMP, HGF, transferrin, insulin, WNT, interleukins, albumin, VEGF, homologs, paralogs, orthologs, variants, precursors, isoforms, and combinations thereof.

Embodiment I-34. The medium of embodiment I-16 or I-33, wherein the growth factor is selected from Table 10.

Embodiment I-35. The medium of embodiment I-16 or I-33, wherein the growth factor is a chicken growth factor, duck growth factor, bovine growth factor, sheep growth factor, fish growth factor, porcine growth factor, mammalian growth factor, avian growth factor, reptile growth factor, amphibian growth factor, arachnid growth factor or teleost growth factor.

Embodiment I-36. The medium as in one of embodiments I-1 to I-35, further comprising an adhesion protein.

Embodiment I-37. The medium as in embodiment I-36 wherein the adhesion protein is selected from Table 14.

Embodiment I-38. The medium as in one of embodiments I-1 to I-37, wherein the plurality of ingredients comprises one or more amino acids at the concentration range shown below:

| Amino Acids | Lowest Concentration (g/L) | Highest Concentration (g/L) |
| --- | --- | --- |
| L-ALANINE | 0.0001 | 0.5 |
| L-ARGININE | 0.01 | 2.5 |
| L-ARGININE HYDROCHLORIDE | 0.01 | 1 |
| L-ASPARAGINE ANHYDROUS | 0.1 | 1.5 |
| L-ASPARAGINE MONOHYDRATE | 0.01 | 0.9 |
| L-CYSTEINE HYDROCHLORIDE | 0.001 | 0.5 |
| L-CYSTINE DIHYDROCHLORIDE | 0.005 | 1.5 |
| L-GLUTAMIC ACID | 0.01 | 1.5 |
| L-GLUTAMIC ACID MONOSODIUM SALT MONOHYDRATE | 0.01 | 1.5 |
| L-GLUTAMINE | 0.14 | 1.5 |
| L-GLYCINE | 0.01 | 0.5 |
| L-HISTIDINE FREE BASE | 0.01 | 0.5 |
| L-HISTIDINE HYDROCHLORIDE | 0.01 | 0.5 |
| HYDROXY-L-PROLINE | 0.01 | 0.25 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-SERINE | 0.1 | 1 |
| L-THREONINE | 0.05 | 0.5 |
| L-TRYPTOPHAN | 0.01 | 0.5 |
| L-TYROSINE DISODIUM SALT DIHYDRATE | 0.01 | 0.5 |
| L-VALINE | 0.1 | 0.75 |
| L-ORNITHINE | 0.001 | 0.05 |
| L-ASPARTIC ACID | 0.1 | 0.8 |
| L-ALPHA-AMINOBUTYRIC ACID | 0.001 | 0.025 |
| GABA | 0.01 | 0.2 |
| L-CARNOSINE | 0.01 | 1 |

Embodiment I-39. The medium as in one of embodiments I-1 to I-38, wherein the plurality of ingredients comprises one or more carbohydrates at the concentration range shown below:

| Carbohydrates | Lowest Concentration (g/L) | Highest Concentration (g/L) |
|---|---|---|
| D-GLUCOSE | 1 | 12 |
| GALACTOSE | 0.1 | 2 |
| MANNOSE | 0.1 | 2 |
| MALTOSE | 0.1 | 2 |
| FUCOSE | 0.1 | 2 |
| SUCROSE | 0.1 | 12 |
| FRUCTOSE | 0.1 | 2 |
| ALLOSE | 0.1 | 2 |
| ALTROSE | 0.1 | 2 |
| GULOSE | 0.1 | 2 |
| IDOSE | 0.1 | 2 |
| TALOSE | 0.1 | 2 |
| PSICOSE | 0.1 | 2 |
| SORBOSE | 0.1 | 2 |
| TAGATOSE | 0.1 | 2 |
| LACTOSE | 0.1 | 2 |
| MYO-INOSITOL | 0.01 | 0.25 |
| RIBOSE | 0.1 | 2 |

Embodiment I-40. The medium as in one of embodiments I-1 to I-39, wherein the plurality of ingredients comprises one or more vitamins at the concentration range shown below:

| Vitamins | Lowest Concentration (g/L) | Highest Concentration (g/L) |
|---|---|---|
| ASCORBIC ACID (Vit C) | 0.0001 | 0.5 |
| D-BIOTIN (Vit B7) | 1.00E−06 | 0.005 |
| ERGOCALCIFEROL (VitD2) | 1.00E−06 | 5.00E−05 |
| FOLIC ACID (Vit B9) | 0.0015 | 0.02 |
| MENADIONE (Vit K3) | 0.00001 | 0.0005 |
| NIACINAMIDE (NICOTINAMIDE) (Vit B3) | 0.001 | 0.01 |
| NIACIN (Vit B3) | 1.00E−06 | 5.00E−02 |
| CALCIUM D-PANTOTHENATE (Vit B5) | 0.0005 | 0.01 |
| PYRIDOXINE HYDROCHLORIDE (Vit B6) | 1.00E−05 | 0.01 |
| RIBOFLAVIN (Vit B2) | 0.0001 | 0.005 |
| THIAMINE HCL (Vit B1) | 0.0025 | 0.05 |
| CYANOCOBALAMIN (Vit B12) | 1.00E−05 | 0.005 |
| DL-ALPHA-TOCOPHEROL (Vit E) | 1.00E−07 | 0.002 |
| D-ALPHA-TOCOPHEROL (Vit E) | 1.00E−07 | 0.002 |
| PARA-AMINO BENZOIC ACID (PABA) | 0.001 | 0.01 |
| PYRIDOXAL HYDROCHLORIDE (Vit B6) | 0.0005 | 0.01 |

Embodiment I-41. The medium as in one of embodiments I-1 to I-40, wherein the plurality of ingredients comprises one or more inorganic salts at the concentration range shown below:

| Inorganic Salts | Lowest Concentration (g/L) | Highest Concentration (g/L) |
|---|---|---|
| CALCIUM CHLORIDE | 0.0005 | 0.2 |
| SODIUM CHLORIDE | 0.1 | 10 |
| SODIUM PHOSPHATE MONOBASIC | 0.01 | 5 |
| SODIUM PHOSPHATE DIBASIC | 0.01 | 5 |
| MAGNESIUM CHLORIDE | 0.0005 | 0.1 |
| MAGNESIUM SULFATE | 0.0005 | 0.1 |
| POTASSIUM CHLORIDE | 0.001 | 1.5 |

Embodiment I-42. The medium as in one of embodiments I-1 to I-41, wherein the plurality of ingredients comprises one or more trace metals at the concentration range shown below:

| Trace Metals | Lowest Concentration (g/L) | Highest Concentration (g/L) |
|---|---|---|
| CADMIUM HEMIPENTAHYDRATE | 0.00000001 | 0.000001 |
| COBALT CHLORIDE | 0.0000001 | 0.00001 |
| AMMONIUM MOLYBDATE | 0.0000001 | 0.0001 |
| SODIUM MOLYBDATE | 0.0000001 | 0.0001 |
| AMMONIUM METAVANADATE | 0.00000001 | 0.000005 |
| SODIUM METAVANADATE | 0.000000001 | 0.000005 |
| STRONTIUM CHLORIDE HEXAHYDRATE | 0.00001 | 0.01 |
| COPPER SULFATE | 2.50E−06 | 0.0025 |
| SODIUM SELENITE | 1.00E−06 | 1.00E−04 |
| SODIUM METASILICATE | 0.00001 | 0.001 |
| CUPRIC CHLORIDE | 1.00E−07 | 0.001 |
| FERRIC AMMONIUM CITRATE | 0.001 | 1 |
| FERROUS SULFATE | 1.00E−05 | 0.001 |
| FERRIC NITRATE | 1.00E−05 | 0.001 |
| NICKLE SULFATE HEXAHYDRATE | 1.00E−07 | 2.00E−06 |
| STANNOUS CHLORIDE DIHYDRATE | 1.00E−07 | 1.00E−06 |
| FERRIC CITRATE | 0.01 | 1 |
| RUBIDIUM CHLORIDE | 1.00E+07 | 5.00E+05 |

Embodiment I-43. The medium as in one of embodiments I-1 to I-42, wherein the plurality of ingredients comprises one or more lipids at the concentration range shown below:

| Lipids | Lowest Concentration (g/L) | Highest Concentration (g/L) |
|---|---|---|
| DL-ALPHA-LIPOIC-ACID | 0.00001 | 0.005 |
| OLEIC ACID | 1.00E−06 | 0.001 |
| CHOLESTEROL | 0.00005 | 0.005 |
| LECITHIN | 1.00E−05 | 0.01 |
| LINOLEIC ACID | 1.00E−05 | 0.005 |
| ARACHIDONIC ACID | 1.00E−08 | 5.00E−05 |
| LINOLENIC ACID | 1.00E−06 | 1.00E−03 |
| MYRISTIC ACID | 1.00E−06 | 1.00E−03 |
| PALMITIC ACID | 1.00E−06 | 1.00E−03 |
| PALMITOLEIC ACID | 1.00E−06 | 1.00E−03 |
| STEARIC ACID | 1.00E−06 | 1.00E−03 |

Embodiment I-44. The medium as in one of embodiments I-1 to I-43, wherein the plurality of ingredients comprises one or more food oils at the concentration range shown below:

| Food oils | Lowest Concentration (g/L) | Highest Concentration (g/L) |
|---|---|---|
| FLAXSEED OIL | 1.00E−06 | 5.00E−03 |
| CANOLA OIL | 1.00E−06 | 5.00E−03 |

-continued

| Food oils | Lowest Concentration (g/L) | Highest Concentration (g/L) |
|---|---|---|
| ALGAL OIL | 1.00E−06 | 5.00E−03 |
| OTHER FOOD OILS | 1.00E−06 | 5.00E−03 |

Embodiment I-45. The medium as in one of embodiments I-1 to I-44, wherein the plurality of ingredients comprises one or more growth factors at the concentration range shown below:

| Growth Factors | Lowest Concentration (g/L) | Highest Concentration (g/L) |
|---|---|---|
| Insulin | 8.00E−04 | 0.008 |
| LR3-IGF1 | 0.009 | 0.04 |
| Transferrin (Holo) | 0.01 | 0.5 |
| FGF-2 | 1.00E−06 | 1.00E−03 |
| FGF-1 | 1.00E−06 | 1.00E−03 |
| PDGF | 1.00E−06 | 1.00E−03 |
| CTGF | 1.00E−06 | 1.00E−03 |
| EGF | 1.00E−06 | 1.00E−03 |
| TGFB | 1.00E−06 | 1.00E−03 |
| BMP | 1.00E−06 | 1.00E−03 |
| HGF | 1.00E−06 | 1.00E−03 |
| KGF | 1.00E−06 | 1.00E−03 |

Embodiment I-46. The medium as in one of embodiments I-1 to I-45, wherein the plurality of ingredients comprises one or more supplementary ingredients at the concentration range shown below:

| Supplementary Ingredients | Lowest Concentration (g/L) | Highest Concentration (g/L) |
|---|---|---|
| HYPOXANTHINE | 0.0001 | 0.01 |
| THYMIDINE | 1.50E−04 | 0.001 |
| TWEEN 80 (POLYSORBATE) | 1.00E−04 | 0.005 |
| PUTRESCINE DIHYDROCHLORIDE | 1.00E−04 | 0.0009 |
| SPERMINE TETRAHYDROCHLORIDE | 1.00E−02 | 0.05 |
| SPERMIDINE | 1.00E−04 | 0.05 |
| CADAVERINE | 1.00E−04 | 0.05 |
| ETHANOLAMINE | 2.00E−03 | 0.08 |
| ETHANOL (ETHYL ALCOHOL) | 6.00E−05 | 1 |
| SODIUM CITRATE | 0.5 | 0.5 |
| SODIUM GLUCONATE | 0.5 | 1.5 |
| METHYL BETA CYCLODEXTRIN | 0.05 | 0.075 |
| L-TAURINE | 0.01 | 0.1 |
| CHOLINE CHLORIDE | 0.001 | 0.5 |

Embodiment I-47. The medium as in one of embodiments I-1 to I-46, wherein the plurality of ingredients comprises one or more TCA cycle intermediates at the concentration range shown below:

| TCA Cycle Intermediates | Lowest Concentration (g/L) | Highest Concentration (g/L) |
|---|---|---|
| SODIUM PYRUVATE | 0.01 | 0.5 |
| SUCCINIC ACID | 0.005 | 1.5 |
| SODIUM SUCCINATE | 0.005 | 0.1 |

Embodiment I-48. The medium as in one of embodiments I-1 to I-47, wherein the plurality of ingredients comprises one or more glycolysis intermediates, iron carriers, ferric maltol, ferrous gluconate, shear protectants, polyethylene glycol, methylcellulose, and hydrolysates.

Embodiment I-49. The medium as in one of embodiments I-1 to I-48, wherein the medium is admixed with water to form a solution.

Embodiment I-50. The medium as in one of embodiments I-1 to I-49, wherein the medium comprises methylcellulose.

Embodiment I-51. The medium as in one of embodiments I-1 to I-50, wherein the medium comprises cyanocobalamin, optionally at a concentration range of 1.00E+05 g/L to 0.0026 g/L.

Embodiment I-52. The medium as in one of embodiments I-1 to I-51, wherein the medium comprises simethicone.

Embodiment I-53. The medium as in one of embodiments I-1 to I-52, wherein the medium comprises ferric ammonium citrate, optionally at a concentration range of 0.01 g/L to 0.5 g/L.

Embodiment I-54. The medium as in one of embodiments I-1 to I-53, wherein the medium comprises food-grade plant oils.

Embodiment I-55. A composition comprising the medium as in one of embodiments I-1 to I-54, further comprising non-human cells in culture.

Embodiment I-56. The composition of embodiment I-55, wherein the cells are from poultry, seafood, game or livestock.

Embodiment I-57. The medium as in one of embodiments I-1 to I-56, wherein the plurality of ingredients comprises one or more amino acids, magnesium salts, sodium salts, copper salts, zinc salts, iron salts, and vitamins.

Embodiment I-58. The medium of embodiment I-57 wherein the ingredients are at the concentration range shown below:

| Ingredients | Lowest Concentration (g/L) | Highest Concentration (g/L) |
|---|---|---|
| L-ARGININE | 0.01 | 2.5 |
| L-CYSTEINE | 0.001 | 0.5 |
| L-CYSTINE | 0.005 | 1.5 |
| L-GLUTAMINE | 0.14 | 1.5 |
| L-HISTIDINE | 0.01 | 0.5 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-TRYPTOPHAN | 0.01 | 0.5 |
| L-TYROSINE | 0.01 | 0.5 |
| L-VALINE | 0.1 | 0.75 |
| D-GLUCOSE | 1 | 12 |
| NIACIN (Vit B3) | 1.00E−06 | 5.00E−02 |
| RIBOFLAVIN | 0.0001 | 0.005 |
| ERGOCALCIFEROL (VitD2) | 1.00E−06 | 5.00E−05 |
| ASCORBIC ACID (Vit C) | 0.0001 | 0.5 |
| COPPER SULFATE | 2.50E−06 | 0.0025 |
| SODIUM SELENITE | 1.00E−06 | 1.00E−04 |
| FERRIC AMMONIUM CITRATE | 0.001 | 1 |
| MAGNESIUM CHLORIDE | 0.0005 | 0.1 |
| MAGNESIUM SULFATE | 0.0005 | 0.1 |
| ZINC SULFATE | 0.00005 | 0.01 |

Embodiment I-59. A universal FGF-2 comprising the amino acid sequence set forth in SEQ ID NO: 3.

Embodiment I-60. A universal FGF-2 encoded by the nucleic acid sequence set forth in SEQ ID NO: 4.

Embodiment I-61. A universal PDGF-BB comprising the amino acid sequence set forth in SEQ ID NO: 5.

Embodiment I-62. A universal IGF-1 comprising the amino acid sequence set forth in SEQ ID NO: 6.

Embodiment I-63. A universal VEGF-A comprising the amino acid sequence as in SEQ ID NO: 7.

Embodiment I-64. A *Gallus* LR3-IGF1 comprising the amino acid sequence set forth in SEQ ID NO: 1.

Embodiment I-65. A method for formulating a medium for culturing cell-based meat comprising:
(a) providing a plurality of ingredients; and
(b) one or more of:
  (i) replacing one or more ingredients currently not approved for use in food with an ingredient approved for use in food;
  (ii) removing one or more ingredients currently not approved for use in food; and
  (iii) formulating one or more ingredients currently not approved for use in food at or below ADI value.

Embodiment I-66. The method of embodiment I-65, wherein the medium is edible.

Embodiment I-67. The method of embodiment I-65 or I-66, wherein the medium contains no more than 10%, 9%, 8%, 7%, 6%, 5%, 4%, 3%, 2%, 1%, 0.5%, 0.1%, 0.05% or no more than 0.01% animal-derived serum.

Embodiment I-68. The method as in one of embodiments I-65 to I-67, wherein the medium is substantially free of animal-derived serum.

Embodiment I-69. The method as in one of embodiments I-65 to I-68, wherein the medium is free of animal-derived serum.

Embodiment I-70. The method as in one of embodiments I-65 to I-69, wherein the medium contains no more than 10%, 9%, 8%, 7%, 6%, 5%, 4%, 3%, 2%, 1%, 0.5%, 0.1%, 0.05% or no more than 0.01%% animal-derived components.

Embodiment I-71. The method as in one of embodiments I-65 to I-70, wherein the medium is substantially free of animal-derived components.

Embodiment I-72. The method as in one of embodiments I-65 to I-71, wherein the medium is free of animal-derived components.

Embodiment I-73. The method as in one of embodiments I-65 to I-72, wherein the medium is chemically defined.

Embodiment I-74. The method as in one of embodiments I-65 to I-73, wherein poloxamer is replaced with methylcellulose.

Embodiment I-75. The method as in one of embodiments I-65 to I-74, wherein cobalt chloride is replaced with cyanocobalamin.

Embodiment I-76. The method as in one of embodiments I-65 to I-75, wherein an anti-foaming agent currently not approved for use in food is replaced with simethicone.

Embodiment I-77. The method as in one of embodiments I-65 to I-76, wherein one or more of ammonium molybdate, sodium molybdate, ammonium metavanadate, sodium metavanadate, rubidium chloride and strontium chloride hexahydrate is replaced with ferric ammonium citrate.

Embodiment I-78. The method as in one of embodiments I-65 to I-77, further comprising adding a growth factor of any one of embodiments I-59 to I-64.

Embodiment II-1. An edible nutrient medium for the production of slaughter-free meat, the medium comprising a plurality of ingredients, wherein each ingredient is approved for use in food and/or is at or below its ADI value.

Embodiment II-2. The medium of embodiment II-1, wherein the ingredient approved for use in food is Generally Recognized As Safe (GRAS).

Embodiment II-3. The medium of embodiment II-1, wherein the medium is substantially free of animal-derived components.

Embodiment II-4. The medium of embodiment II-1, wherein the medium is substantially free of animal-derived serum.

Embodiment II-5. The medium of embodiment II-1, further comprising a growth factor.

Embodiment II-6. The medium of embodiment II-5, wherein the growth factor is a universal growth factor selected from the group consisting of universal FGF-2 (SEQ ID NO: 3), universal PDGF-BB (SEQ ID NO: 5), universal IGF-1 (SEQ ID NO: 6), and universal VEGF-A (SEQ ID NO: 7) or a sequence having at least about 50%, at least about 60%, at least about 70%, at least about 80%, at least about 90%, at least about 95%, at least about 96%, at least about 97%, at least about 98%, at least about 99% sequence identity thereto.

Embodiment II-7. The medium of embodiment II-6, wherein the medium comprises a cis growth factor, wherein the cis growth factor matches the genus of origin of the meat being produced.

Embodiment II-8. The medium of embodiment II-7, wherein the use of the cis growth factor allows for enhanced meat production compared to a non-cis growth factor.

Embodiment II-9. The medium of embodiment II-8, where the cis growth factor is cis *Gallus* transferrin.

Embodiment II-10. The medium of embodiment II-7, wherein the cis growth factor is a variant of the corresponding naturally existing growth factor of the genus of the meat being produced.

Embodiment II-11. The medium of embodiment II-10, wherein the cis growth factor variant is *Gallus* LR3-IGF1, optionally comprising an amino acid sequence set forth in SEQ ID NO: 1.

Embodiment II-12. The medium of embodiment II-5, wherein the growth factor is selected from the group consisting of IGF-1, LR3-IGF1, FGF-1, FGF-2, PDGF, CTGF, EGF, TGFB, BMP, HGF, transferrin, insulin, WNT, interleukins, albumin, VEGF, homologs, paralogs, orthologs, variants, precursors, isoforms, and combinations thereof.

Embodiment II-13. The medium of embodiment II-5, wherein the growth factor is selected from Table 10.

Embodiment II-14. The medium of embodiment II-5, wherein the growth factor is a chicken growth factor, duck growth factor, bovine growth factor, sheep growth factor, fish growth factor, porcine growth factor, mammalian growth factor, avian growth factor, reptile growth factor, amphibian growth factor, arachnid growth factor or teleost growth factor.

Embodiment II-15. The medium of embodiment II-1, further comprising an adhesion protein selected from Table 14.

Embodiment II-16. The medium of embodiment II-1, wherein the plurality of ingredients comprises one or more amino acids at the concentration range shown below:

| Amino Acids | Lowest Concentration (g/L) | Highest Concentration (g/L) |
| --- | --- | --- |
| L-ALANINE | 0.0001 | 0.5 |
| L-ARGININE | 0.01 | 2.5 |
| L-ARGININE HYDROCHLORIDE | 0.01 | 1 |
| L-ASPARAGINE ANHYDROUS | 0.1 | 1.5 |
| L-ASPARAGINE MONOHYDRATE | 0.01 | 0.9 |
| L-CYSTEINE HYDROCHLORIDE | 0.001 | 0.5 |
| L-CYSTINE DIHYDROCHLORIDE | 0.005 | 1.5 |
| L-GLUTAMIC ACID | 0.01 | 1.5 |
| L-GLUTAMIC ACID | 0.01 | 1.5 |

-continued

| Amino Acids | Lowest Concentration (g/L) | Highest Concentration (g/L) |
|---|---|---|
| MONOSODIUM SALT MONOHYDRATE | | |
| L-GLUTAMINE | 0.14 | 1.5 |
| L-GLYCINE | 0.01 | 0.5 |
| L-HISTIDINE FREE BASE | 0.01 | 0.5 |
| L-HISTIDINE HYDROCHLORIDE | 0.01 | 0.5 |
| HYDROXY-L-PROLINE | 0.01 | 0.25 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-SERINE | 0.1 | 1 |
| L-THREONINE | 0.05 | 0.5 |
| L-TRYPTOPHAN | 0.01 | 0.5 |
| L-TYROSINE DISODIUM SALT DIHYDRATE | 0.01 | 0.5 |
| L-VALINE | 0.1 | 0.75 |
| L-ORNITHINE | 0.001 | 0.05 |
| L-ASPARTIC ACID | 0.1 | 0.8 |
| L-ALPHA-AMINOBUTYRIC ACID | 0.001 | 0.025 |
| GABA | 0.01 | 0.2 |
| L-CARNOSINE | 0.01 | 1 |

Embodiment II-17. The medium of embodiment II-1, wherein the plurality of ingredients comprises one or more carbohydrates at the concentration range shown below:

| Carbohydrates | Lowest Concentration (g/L) | Highest Concentration (g/L) |
|---|---|---|
| D-GLUCOSE | 1 | 12 |
| GALACTOSE | 0.1 | 2 |
| MANNOSE | 0.1 | 2 |
| MALTOSE | 0.1 | 2 |
| FUCOSE | 0.1 | 2 |
| SUCROSE | 0.1 | 12 |
| FRUCTOSE | 0.1 | 2 |
| ALLOSE | 0.1 | 2 |
| ALTROSE | 0.1 | 2 |
| GULOSE | 0.1 | 2 |
| IDOSE | 0.1 | 2 |
| TALOSE | 0.1 | 2 |
| PSICOSE | 0.1 | 2 |
| SORBOSE | 0.1 | 2 |
| TAGATOSE | 0.1 | 2 |
| LACTOSE | 0.1 | 2 |
| MYO-INOSITOL | 0.01 | 0.25 |
| RIBOSE | 0.1 | 2 |

Embodiment II-18. The medium of embodiment II-1, wherein the plurality of ingredients comprises one or more vitamins at the concentration range shown below:

| Vitamins | Lowest Concentration (g/L) | Highest Concentration (g/L) |
|---|---|---|
| ASCORBIC ACID (Vit C) | 0.0001 | 0.5 |
| D-BIOTIN (Vit B7) | 1.00E-06 | 0.005 |
| ERGOCALCIFEROL (VitD2) | 1.00E-06 | 5.00E-05 |
| FOLIC ACID (Vit B9) | 0.0015 | 0.02 |
| MENADIONE (Vit K3) | 0.00001 | 0.0005 |
| NIACINAMIDE(NICOTINAMIDE) (Vit B3) | 0.001 | 0.01 |
| NIACIN (Vit B3) | 1.00E-06 | 5.00E-02 |
| CALCIUM D-PANTOTHENATE (Vit B5) | 0.0005 | 0.01 |
| PYRIDOXINE HYDROCHLORIDE (Vit B6) | 1.00E-05 | 0.01 |
| RIBOFLAVIN (Vit B2) | 0.0001 | 0.005 |
| THIAMINE HCL (Vit B1) | 0.0025 | 0.05 |
| CYANOCOBALAMIN (Vit B12) | 1.00E-05 | 0.005 |
| DL-ALPHA-TOCOPHEROL (Vit E) | 1.00E-07 | 0.002 |
| D-ALPHA-TOCOPHEROL (Vit E) | 1.00E-07 | 0.002 |
| PARA-AMINO BENZOIC ACID (PABA) | 0.001 | 0.01 |
| PYRIDOXAL HYDROCHLORIDE (Vit B6) | 0.0005 | 0.01 |

Embodiment II-19. The medium of embodiment II-1, wherein the plurality of ingredients comprises one or more inorganic salts at the concentration range shown below:

| Inorganic Salts | Lowest Concentration (g/L) | Highest Concentration (g/L) |
|---|---|---|
| CALCIUM CHLORIDE | 0.0005 | 0.2 |
| SODIUM CHLORIDE | 0.1 | 10 |
| SODIUM PHOSPHATE MONOBASIC | 0.01 | 5 |
| SODIUM PHOSPHATE DIBASIC | 0.01 | 5 |
| MAGNESIUM CHLORIDE | 0.0005 | 0.1 |
| MAGNESIUM SULFATE | 0.0005 | 0.1 |
| POTASSIUM CHLORIDE | 0.001 | 1.5 |

Embodiment II-20. The medium of embodiment II-1, wherein the plurality of ingredients comprises one or more trace metals at the concentration range shown below:

| Trace Metals | Lowest Concentration (g/L) | Highest Concentration (g/L) |
| --- | --- | --- |
| CADMIUM HEMIPENTAHYDRATE | 0.00000001 | 0.000001 |
| COBALT CHLORIDE | 0.0000001 | 0.00001 |
| AMMONIUM MOLYBDATE | 0.0000001 | 0.0001 |
| SODIUM MOLYBDATE | 0.0000001 | 0.0001 |
| AMMONIUM METAVANADATE | 0.00000001 | 0.000005 |
| SODIUM METAVANADATE | 0.000000001 | 0.000005 |
| STRONTIUM CHLORIDE HEXAHYDRATE | 0.00001 | 0.01 |
| COPPER SULFATE | 2.50E−06 | 0.0025 |
| SODIUM SELENITE | 1.00E−06 | 1.00E−04 |
| SODIUM METASILICATE | 0.00001 | 0.001 |
| CUPRIC CHLORIDE | 1.00E−07 | 0.001 |
| FERRIC AMMONIUM CITRATE | 0.001 | 1 |
| FERROUS SULFATE | 1.00E−05 | 0.001 |
| FERRIC NITRATE | 1.00E−05 | 0.001 |
| NICKLE SULFATE HEXAHYDRATE | 1.00E−07 | 2.00E−06 |
| STANNOUS CHLORIDE DIHYDRATE | 1.00E−07 | 1.00E−06 |
| FERRIC CITRATE | 0.01 | 1 |
| RUBIDIUM CHLORIDE | 1.00E+07 | 5.00E+05 |

Embodiment II-21. The medium of embodiment II-1, wherein the plurality of ingredients comprises one or more lipids at the concentration range shown below:

| Lipids | Lowest Concentration (g/L) | Highest Concentration (g/L) |
| --- | --- | --- |
| DL-ALPHA-LIPOIC-ACID | 0.00001 | 0.005 |
| OLEIC ACID | 1.00E−06 | 0.001 |
| CHOLESTEROL | 0.00005 | 0.005 |
| LECITHIN | 1.00E−05 | 0.01 |
| LINOLEIC ACID | 1.00E−05 | 0.005 |
| ARACHIDONIC ACID | 1.00E−08 | 5.00E−05 |
| LINOLENIC ACID | 1.00E−06 | 1.00E−03 |
| MYRISTIC ACID | 1.00E−06 | 1.00E−03 |
| PALMITIC ACID | 1.00E−06 | 1.00E−03 |
| PALMITOLEIC ACID | 1.00E−06 | 1.00E−03 |
| STEARIC ACID | 1.00E−06 | 1.00E−03 |

Embodiment II-22. The medium of embodiment II-1, wherein the plurality of ingredients comprises one or more food oils at the concentration range shown below:

| Food oils | Lowest Concentration (g/L) | Highest Concentration (g/L) |
| --- | --- | --- |
| FLAXSEED OIL | 1.00E−06 | 5.00E−03 |
| CANOLA OIL | 1.00E−06 | 5.00E−03 |
| ALGAL OIL | 1.00E−06 | 5.00E−03 |
| OTHER FOOD OILS | 1.00E−06 | 5.00E−03 |

Embodiment II-23. The medium of embodiment II-1, wherein the plurality of ingredients comprises one or more growth factors at the concentration range shown below:

| Growth Factors | Lowest Concentration (g/L) | Highest Concentration (g/L) |
| --- | --- | --- |
| Insulin | 8.00E−04 | 0.008 |
| LR3-IGF1 | 0.009 | 0.04 |
| Transferrin (Holo) | 0.01 | 0.5 |
| FGF-2 | 1.00E−06 | 1.00E−03 |
| FGF-1 | 1.00E−06 | 1.00E−03 |
| PDGF | 1.00E−06 | 1.00E−03 |
| CTGF | 1.00E−06 | 1.00E−03 |
| EGF | 1.00E−06 | 1.00E−03 |
| TGFB | 1.00E−06 | 1.00E−03 |
| BMP | 1.00E−06 | 1.00E−03 |
| HGF | 1.00E−06 | 1.00E−03 |
| KGF | 1.00E−06 | 1.00E−03 |

Embodiment II-24. The medium of embodiment II-1, wherein the plurality of ingredients comprises one or more supplementary ingredients at the concentration range shown below:

| Supplementary Ingredients | Lowest Concentration (g/L) | Highest Concentration (g/L) |
| --- | --- | --- |
| HYPOXANTHINE | 0.0001 | 0.01 |
| THYMIDINE | 1.50E−04 | 0.001 |
| TWEEN 80 (POLYSORBATE) | 1.00E−04 | 0.005 |
| PUTRESCINE DIHYDROCHLORIDE | 1.00E−04 | 0.0009 |
| SPERMINE TETRAHYDROCHLORIDE | 1.00E−02 | 0.05 |
| SPERMIDINE | 1.00E−04 | 0.05 |
| CADAVERINE | 1.00E−04 | 0.05 |
| ETHANOLAMINE | 2.00E−03 | 0.08 |
| ETHANOL (ETHYL ALCOHOL) | 6.00E−05 | 1 |
| SODIUM CITRATE | 0.5 | 0.5 |
| SODIUM GLUCONATE | 0.5 | 1.5 |
| METHYL BETA CYCLODEXTRIN | 0.05 | 0.075 |
| L-TAURINE | 0.01 | 0.1 |
| CHOLINE CHLORIDE | 0.001 | 0.5 |

Embodiment II-25. The medium of embodiment II-1, wherein the plurality of ingredients comprises one or more TCA cycle intermediates at the concentration range shown below:

| TCA Cycle Intermediates | Lowest Concentration (g/L) | Highest Concentration (g/L) |
| --- | --- | --- |
| SODIUM PYRUVATE | 0.01 | 0.5 |
| SUCCINIC ACID | 0.005 | 1.5 |
| SODIUM SUCCINATE | 0.005 | 0.1 |

Embodiment II-26. The medium of embodiment II-1, wherein the plurality of ingredients comprises one or more glycolysis intermediates, iron carriers, ferric maltol, ferrous gluconate, shear protectants, polyethylene glycol, methylcellulose, simethicone, food-grade plant oils and hydrolysates.

Embodiment II-27. The medium of embodiment II-1 wherein the ingredients are at the concentration range shown below:

| Ingredients | Lowest Concentration (g/L) | Highest Concentration (g/L) |
|---|---|---|
| L-ARGININE | 0.01 | 2.5 |
| L-CYSTEINE | 0.001 | 0.5 |
| L-CYSTINE | 0.005 | 1.5 |
| L-GLUTAMINE | 0.14 | 1.5 |
| L-HISTIDINE | 0.01 | 0.5 |
| L-ISOLEUCINE | 0.1 | 0.75 |
| L-LEUCINE | 0.01 | 0.75 |
| L-LYSINE | 0.01 | 1 |
| L-METHIONINE | 0.05 | 0.5 |
| L-PHENYLALANINE | 0.05 | 0.5 |
| L-PROLINE | 0.1 | 1 |
| L-TRYPTOPHAN | 0.01 | 0.5 |
| L-TYROSINE | 0.01 | 0.5 |
| L-VALINE | 0.1 | 0.75 |
| D-GLUCOSE | 1 | 12 |
| NIACIN (Vit B3) | 1.00E−06 | 5.00E−02 |
| RIBOFLAVIN | 0.0001 | 0.005 |
| ERGOCALCIFEROL (VitD2) | 1.00E−06 | 5.00E−05 |
| ASCORBIC ACID (Vit C) | 0.0001 | 0.5 |
| COPPER SULFATE | 2.50E−06 | 0.0025 |
| SODIUM SELENITE | 1.00E−06 | 1.00E−04 |
| FERRIC AMMONIUM CITRATE | 0.001 | 1 |
| MAGNESIUM CHLORIDE | 0.0005 | 0.1 |
| MAGNESIUM SULFATE | 0.0005 | 0.1 |
| ZINC SULFATE | 0.00005 | 0.01 |

Embodiment II-28. A universal growth factor selected from the group consisting of universal FGF-2 (SEQ ID NO: 3), universal PDGF-BB (SEQ ID NO: 5), universal IGF-1 (SEQ ID NO: 6), and universal VEGF-A (SEQ ID NO: 7) or a sequence having at least about 50%, at least about 60%, at least about 70%, at least about 80%, at least about 90%, at least about 95%, at least about 96%, at least about 97%, at least about 98%, at least about 99% sequence identity thereto.

Embodiment II-29. A *Gallus* LR3-IGF1 comprising the amino acid sequence set forth in SEQ ID NO: 1 or a sequence having at least about 50%, at least about 60%, at least about 70%, at least about 80%, at least about 90%, at least about 95%, at least about 96%, at least about 97%, at least about 98%, at least about 99% sequence identity thereto.

Embodiment II-30. A method for formulating a nutrient medium for the production of slaughter-free meat comprising:
(a) providing a plurality of ingredients; and
(b) one or more of:
  (i) replacing one or more ingredients currently not approved for use in food with an ingredient approved for use in food;
  (ii) removing one or more ingredients currently not approved for use in food; and
  (iii) formulating one or more ingredients currently not approved for use in food at or below ADI value.

Embodiment II-31. The method of embodiment II-30 wherein the replacing one or more ingredients currently not approved for use in food with an ingredient approved for use in food, comprises one or more of:

a. wherein poloxamer is replaced with methylcellulose;
b. wherein cobalt chloride is replaced with cyanocobalamin;
b. wherein an anti-foaming agent currently not approved for use in food is replaced with simethicone; and
c. wherein one or more ammonium molybdate, sodium molybdate, ammonium metavanadate, sodium metavanadate, rubidium chloride and strontium chloride hexahydrate is replaced with ferric ammonium citrate.

Embodiment II-32. The method of embodiment II-30, wherein poloxamer is replaced with methylcellulose.

Embodiment II-33. The method of embodiment II-30, wherein cobalt chloride is replaced with cyanocobalamin.

Embodiment II-34. The method of embodiment II-30, wherein an anti-foaming agent currently not approved for use in food is replaced with simethicone.

Embodiment II-35. The method of embodiment II-30, wherein one or more of ammonium molybdate, sodium molybdate, ammonium metavanadate, and sodium metavanadate is replaced with ferric ammonium citrate.

EXAMPLES

Example 1. Growth of Adherent *Gallus* Cells in Cell Culture Medium Containing GRAS Vs Non-GRAS Ingredients Adherent *Gallus* cells were thawed and seeded at a density of 5000 cells/cm$^2$ in a T25-flask. Three media were prepared according to standard media hydration protocols. Dry powder media was added to DI water in clean vessels and allowed to stir until all components were dissolved. The pH and osmolality of the media were adjusted to 7.4 and 300 mOsm/kg respectively. Media were then filtered using 0.22 nm PES filtration units and stored at 4° C. until use. Prior to use, the media were allowed to come up to room temperature. Three different media conditions were prepared, (1) an exemplary animal component free cell-medium of the present disclosure media hydrated without chemical components which lack a GRAS designation for food applications, or which do not have a GRAS designation (GRAS-ACF), (2) a serum free cell culture medium containing Non-GRAS certified ingredients (Non-GRAS SF), and (3) negative control. Test conditions were seeded in triplicate in 6-well plates at a density of 5000 cells/cm$^2$. Cells were incubated at 39° C. in 5% $CO_2$ in a Biotek BioSpa Live Cell Analysis System (BioSpa) for over five days. Cells were imaged every 12 hours using the BioSpa. Images were processed using BioTeck Gen5 Data Analysis software. Data was then exported and analyzed using Microsoft Excel and SAS JMP.

FIG. 1A shows the mean number of viable adherent cells counted with time. Cells grown in the GRAS-ACF media displayed faster growth rate than cells grown in Non-GRAS SF media. Minimal cell growth was seen in the negative control.

Example 2. Growth of Suspension *Gallus* Cells in Cell Culture Medium Containing GRAS Vs Non-GRAS Ingredients Suspension *Gallus* cells were thawed and seeded at a density of 0.25×10$^6$ cells/mL in 125 mL erlenmeyer cell culture flasks. Cells were placed in a 39° C. shaking incubator with 5% $CO_2$ with a rotation speed of 125 RPM. Two media were prepared according to standard media hydration protocols. Dry powder media was added to DI water in clean vessels and allowed to stir until all components were dissolved. The pH and osmolality of the media were adjusted to 7.4 and 300 mOsm/kg respectively. Media were then filtered using 0.22 μm PES filtration units and stored at 4° C. until use. Prior to use, the media were allowed to come up to room temperature. Two different media conditions were prepared, (1) an exemplary animal component free cell-medium of the present disclosure media hydrated without chemical components which lack a GRAS designation for food applications, or which do not have a GRAS designation (GRAS-ACF) and (2) a serum free cell culture medium containing Non-GRAS certified ingredients (Non-GRAS SF). Test conditions were seeded in duplicate in 125 mL erlenmeyer cell culture flasks at a density of 0.25×10$^6$ cells/mL. Cells were incubated for 4 days. Samples were taken daily using aseptic technique and then counted using a Beckman-Coulter Vi-CELL XR. Data was exported and analyzed using Microsoft Excel and SAS JMP.

FIG. 1B shows the mean number of viable suspension cells counted with time. Similar to adherent cells described in Example 1, the suspension cells grown in GRAS-ACF media displayed a higher growth rate than those grown in Non-GRAS SF media. A sharp decline in cell viability was observed at day 4 for cells grown in Non-GRAS SF media while a continued growth was observed for GRAS-ACF media.

Examples 1 and 2 demonstrate the ability of exemplary animal component free cell culture media of the present disclosure containing GRAS certified ingredients to support growth of both adherent and suspensions cells compared to cell media containing potentially hazardous Non-GRAS certified ingredients.

Example 3. Comparison of Suspension Cell Growth in Commercially Available Media Vs an Optimized Media Suspension *Gallus* cells were thawed and seeded at a density of 0.25×10$^6$ cells/mL in 125 mL erlenmeyer cell culture flasks. Cells were placed in a 39° C. shaking incubator with 5% CO$_2$ with a rotation speed of 125 RPM. Cells were incubated using two different media conditions (1) a commercially available medium (commercial media) and (2) an exemplary animal component free cell-medium of the present disclosure (optimized media). Media was prepared according to standard media hydration protocols. Dry powder media was added to DI water in a clean vessel and allowed to stir until all components were dissolved. The pH and osmolality of the medium was adjusted to 7.4 and 300 mOsm/kg respectively. The medium was then filtered using a 0.22 μm PES filtration unit and stored at 4° C. until use. Test conditions were seeded in duplicate. Cells were incubated for 5 days. Samples were taken daily using aseptic technique and then counted using a Beckman-Coulter Vi-CELL XR. Data was exported and analyzed using Microsoft Excel and SAS JMP.

FIG. 2 illustrates the number of viable cells grown in optimized media vs. in a commercial media over 5 days. A clear increase in viable cell population was observed for cells grown in the optimized media. The higher cell viability was sustained till the end of the experiment, which demonstrates the enhanced cell growth performance of an optimized cell culture medium of the present disclosure over a commercially available cell culture medium.

Example 4. Generation of Universal Recombinant Growth Factors

By way of example, the production of universal recombinant FGF-2, PDGF-BB, VEGF-A, and IGF-1 are described below.

Universal FGF-2

A universal FGF-2 was constructed using the most common amino acid residues at each site according to Uniprot alignment program https://www.uniprot.org/. FGF-2 sequences were chosen from several common mammalian, amphibian and avian species including mouse, rat, chicken, bovine, human, chimpanzee, sheep, *xenopus*, dog, ferret, cat and horse. The canonical amino acids that reflect the most common choice of amino acid at each position is shown in the amino acid sequence shown in SEQ ID NO:3 (Table 13).

Cloning of universal FGF-2 into the *E. coli* expression vector pET32a (+) was done following Soleyman et al. High-level Expression and Purification of Active Human FGF-2 in *Escherichia coli* by Codon and Culture Condition Optimization Iran Red Crescent Med J. 2016 February; 18(2): e21615. The amino acid sequence was codon optimized for *E. coli* BL21 (DE3) expression. The DNA sequence for the universal FGF-2 (SEQ ID NO:4, Table 13) was submitted for total gene synthesis and included PCR nucleotide sequences designed by NEB Builder to insert the sequence into PET32a(+) using NEBuilder® HiFi DNA Assembly Master Mix/NEBuilder HiFi DNA Assembly Cloning Kit per manufacturer's instructions.

Universal PDGF-BB

A universal PDGF-BB was constructed using the same method as described above for universal FGF-2. The amino acid sequence for universal PDGF-BB is shown in SEQ ID NO: 5 (Table 13).

Universal IGF-1 and Universal VEGF-A

Universal IGF-1 and Universal VEGF-A were constructed using a similar method as described above for universal FGF-2 with some variations. The amino acid sequence for universal IGF-1 and universal VEGF-A are shown in SEQ ID NO. 6 and SEQ ID NO. 7, respectively (Table 13). Clustal Omega multiple sequence alignment program was used, https://www.ebi.ac.uk/Tools/msa/clustalo/. IGF-1 and VEGF-A sequences were chosen from species including human, bovine, pig, sheep, goat and chicken. The universal growth factors sequences were determined from EMBOSS Cons tool, to determine the consensus amino acid residue at each location, https://www.ebi.ac.uk/Tools/msa/emboss_cons/.

Example 5. Production of Species-Specific Cis Recombinant Growth Factors

Species-specific cis growth factors for the purpose of growing cultured-meat of the same genus/species were recombinantly produced in *E. coli* or mammalian cells. By way of example, recombinant production of *Gallus* FGF-2 for use in culture of cell-based chicken is described below.

DNA encoding for *Gallus* FGF-2 was codon optimized for bacterial expression. The DNA was then inserted into a bacterial expression vector, such as PET32a. The vector carrying the gene coding for the cis growth factor was expressed in *E. coli* and optimized for protein production and purification. Bioactivity of the purified protein was determined by proliferation assay in growth factor sensitive cells, such as NIH3T3 fibroblasts. The purified growth factor was then used in cell cultures to facilitate the production of cell-based meat.

Example 6. Cellular Response to Cis Recombinant *Gallus* FGF-2 Compared to Commercial Human Recombinant FGF-2

Adherent *Gallus* cells were thawed and seeded at a density of 5000 cells/cm$^2$ in a T25-flask. One medium was prepared according to standard media hydration protocols. Dry powder media was added to DI water in a clean vessel and allowed to stir until all components were dissolved. The pH and osmolality of the medium were adjusted to 7.4 and 300 mOsm/kg respectively. The medium was then filtered using a 0.22 μm PES filtration unit and stored at 4° C. until use. Prior to use, the medium was allowed to come up to room temperature. Cells were seeded in the inner wells of a 96-well cell culture plate. Wells were either seeded with one of two different FGF-2 growth factors, a recombinant *Gallus* FGF-2 produced as described in Example 5, or a commercially available recombinant human FGF-2, or without any growth factors. Each growth factor was seeded at two different concentrations, 10 μg/L or 100 μg/L. Test conditions were all seeded in triplicate at a density of 5000 cells/cm$^2$. Cells were incubated at 39° C. in 5% $CO_2$ in a Biotek BioSpa Live Cell Analysis System (BioSpa) for five days. Cells were imaged every 12 hours using the BioSpa. Images were processed using BioTeck Gen5 Data Analysis software. Data was then exported and analyzed using Microsoft Excel and SAS JMP.

FIG. 3 shows the cellular response for cis *Gallus* FGF-2 and commercial human FGF-2 at 10 μg/L and 100 μg/L compared to media with no growth factor (blank). The results demonstrate equivalent activity of *Gallus* cells grown with cis *Gallus* FGF-2 as those with commercially human FGF-2 at both concentrations tested. These results demonstrate the applicability of the recombinant growth factors of the present disclosure for growing species-matched cis cell-based meat without any loss of function compared to widely available commercial growth factors.

Example 7. Growth of Adherent *Gallus* Cells in Cell Culture Medium Comprising Cis *Gallus* Transferrin Vs. Human Recombinant Transferrin Adherent *Gallus* cells were thawed and seeded at a density of 5000 cells/cm$^2$ in a T25-flask. Three media were prepared according to standard media hydration protocols. Dry powder media was added to DI water in clean vessels and allowed to stir until all components were dissolved. The pH and osmolality of the media were adjusted to 7.4 and 300 mOsm/kg respectively. Media were then filtered using 0.22 μm PES filtration units and stored at 4° C. until use. Prior to use, the media were allowed to come up to room temperature. Three different media conditions were prepared, (1) an exemplary serum free cell-medium of the present disclosure media hydrated with human recombinant transferrin, (2) a serum free cell culture medium hydrated with *Gallus* (chicken) transferrin, and (3) a positive control media hydrated with human recombinant transferrin and a commercial serum replacement product. Test conditions were seeded in 96-well plates at a density of 5000 cells/cm$^2$. Cells were incubated at 39° C. in 5% $CO_2$ in a Biotek BioSpa Live Cell Analysis System (BioSpa) for five days. Cells were imaged after 7 days using the BioSpa. Images were processed using BioTeck Gen5 Data Analysis software. Data was then exported and analyzed using Microsoft Excel and SAS JMP.

FIG. 4 is a bar chart showing cell count as the percentage of the control for each condition. *Gallus* cells grown with cis *Gallus* transferrin in the media clearly displayed higher cell counts at all tested concentrations compared to cells grown with human recombinant transferrin in the media.

The invention claimed is:

1. A method for formulating an edible nutrient medium for the production of slaughter-free meat for human consumption, comprising:
   (a) providing a plurality of ingredients including
      (i) one or more of cyanocobalamin, an edible anti-foaming agent, and ferric ammonium citrate; and
      (ii) one or more of IGF-1, LR3-IGF1, FGF-1, FGF-2, PDGF, CTGF, EGF, TGFB, BMP, HGF, transferrin, insulin, WNT proteins, interleukins, albumin, VEGF, and homologs thereof; and
   (b) mixing the plurality of ingredients in water to form the edible nutrient medium; wherein the nutrient medium does not comprise cobalt chloride, ammonium molybdate, ammonium metavanadate, sodium metavanadate, rubidium chloride, and strontium chloride hexahydrate; thereby forming an edible nutrient medium for culturing an animal cell line suitable for the production of slaughter-free meat.

2. The method of claim 1, wherein the nutrient medium further comprises 8 or more amino acids selected from those below and within concentration ranges shown below:

| Amino Acids | Lowest Concentration (g/L) | Highest Concentration (g/L) |
| --- | --- | --- |
| L-alanine | 0.0001 | 0.5 |
| L-arginine | 0.01 | 2.5 |
| L-arginine hydrochloride | 0.01 | 1 |
| L-asparagine anhydrous | 0.1 | 1.5 |
| L-asparagine monohydrate | 0.01 | 0.9 |
| L-cysteine hydrochloride | 0.001 | 0.5 |
| L-cystine dihydrochloride | 0.005 | 1.5 |
| L-glutamic acid | 0.01 | 1.5 |
| L-glutamic acid monosodium salt monohydrate | 0.01 | 1.5 |
| L-glutamine | 0.14 | 1.5 |
| L-glycine | 0.01 | 0.5 |
| L-histidine free base | 0.01 | 0.5 |
| L-histidine hydrochloride | 0.01 | 0.5 |
| hydroxy-L-proline | 0.01 | 0.25 |
| L-isoleucine | 0.1 | 0.75 |
| L-leucine | 0.01 | 0.75 |
| L-lysine | 0.01 | 1 |
| L-methionine | 0.05 | 0.5 |
| L-phenylalanine | 0.05 | 0.5 |
| L-proline | 0.1 | 1 |
| L-serine | 0.1 | 1 |
| L-threonine | 0.05 | 0.5 |
| L-tryptophan | 0.01 | 0.5 |
| L-tyrosinedisodium saltdihydrate | 0.01 | 0.5 |
| L-valine | 0.1 | 0.75 |
| L-ornithine | 0.001 | 0.05 |
| L-aspartic acid | 0.1 | 0.8 |
| L-alpha-aminobutyric acid | 0.001 | 0.025 |
| Gaba | 0.01 | 0.2 |
| l-carnosine | 0.01 | 1. |

3. The method of claim 1, further comprising providing plant derived oils or yeast hydrolysates to the nutrient medium, wherein the nutrient medium does not comprise DL-alpha lipoic acid.

4. The method of claim 1, wherein the nutrient medium does not comprise: one or more category 3 ingredients selected from: bovine transferrin, chicken serum, and bovine serum; and
   the plurality of ingredients includes d-glucose, folic acid, dl-alpha-tocopherol acetate, vitamin d2, d-alpha-tocopherol, d-biotin, myo-lnositol, niacinamide, pyridoxine-hcl, pyri doxal-hcl, riboflavin, thiamine-hcl, vitamin b12, calcium d-pantothenate, choline chloride, ascorbic acid, sodium chloride, calcium chloride, manganese sulfate H2O, potassium chloride, magnesium chloride, copper sulfate-pentahydrate, sodium metasilicate-9H2O, zinc sulfate-7H2O, magnesium sulfate, sodium phosphate monobasic H2O, sodium phosphate dibasic, 1-alanine, 1-arginine-hcl, 1-asparagine-H2O, l-aspartic acid, l-cysteine hcl H2O, l-cystine 2hcl, l-glutamic acid monosodium H2O, l-glutamine, glycine, l-histidine-hcl-H2O, l-isoleucine, l-leucine, l-lysine-hcl, l-methionine, l-phenylalanine, l-proline, l-serine, l-threonine, l-tryptophan, 1-tyrosine-2na-2H2O, l-valine, succinic acid, sodium succinate-2na 6H2O, sodium selenite (anhy), ferrous sulfate-7H2O, ferric citrate, ferric ammonium citrate, linoleic acid, monoethanola mine, tween 80, l-glutathione, and hypep 2 yeast extract.

5. The method of claim 1, wherein the nutrient medium does not comprise: rubidium chloride, strontium chloride hexahydrate, hypoxanthine, putrescine, thymidine, and DL-alpha-lipoic acid.

6. The method of claim 1, wherein the nutrient medium does not comprise: chicken serum and bovine serum.

7. The method of claim 1, wherein the nutrient medium does not comprise any animal-derived component nor any animal-derived serum.

8. The method of claim 1, wherein the plurality of ingredients includes one or more of glycolysis intermediates, iron carriers, ferric maltol, ferrous gluconate, shear protectants, polyethylene glycol, methylcellulose, simethicone, food-grade plant oils, and hydrolysates.

9. The method of claim 1, wherein the plurality of ingredients includes one or more of an adhesion protein selected from Vitronectin; Collagen alpha-3(IV); Collagen, type IV, alpha I; TPA: fibronectin; and Fibronectin, partial.

10. The method of claim 1, wherein:
   (a) the nutrient medium does not comprise poloxamer;
   (b) the plurality of ingredients includes methylcellulose in an amount to provide shear protection; and
   (c) the plurality of ingredients includes cyanocobalamin to provide an essential cofactor.

11. The method of claim 1, wherein the plurality of ingredients includes glycolysis intermediates, shear protectants, polyethylene glycol, methylcellulose, food-grade plant oils, hydrolysates, and one or more of iron carriers, ferric maltol, ferrous gluconate, and an adhesion protein selected from Vitronectin; Collagen alpha-3(IV); Collagen, type IV, alpha I; TPA: fibronectin; and Fibronectin, partial.

12. A method for formulating an edible nutrient medium for the production of cultured meat for human consumption, comprising:
   (a) providing a plurality of ingredients including one or more of cyanocobalamin, an edible anti-foaming agent, and ferric ammonium citrate; and
   (b) mixing the plurality of ingredients in water to form the edible nutrient medium; wherein the nutrient medium does not comprise cobalt chloride, ammonium molybdate, ammonium metavanadate, sodium metavanadate, rubidium chloride, strontium chloride hexahydrate, animal-derived components, and animal-derived serums.

13. The method of claim 12, wherein the plurality of ingredients includes two or more of cyanocobalamin, an edible anti-foaming agent, and ferric ammonium citrate.

14. The method of claim 12, wherein the plurality of ingredients includes methylcellulose.

15. The method of claim 12, wherein the nutrient medium further comprises 8 or more amino acids selected from those below and within concentration ranges shown below:

| Amino Acids | Lowest Concentration (g/L) | Highest Concentration (g/L) |
| --- | --- | --- |
| L-alanine | 0.0001 | 0.5 |
| L-arginine | 0.01 | 2.5 |
| L-arginine hydrochloride | 0.01 | 1 |
| L-asparagine anhydrous | 0.1 | 1.5 |
| L-asparagine monohydrate | 0.01 | 0.9 |
| L-cysteine hydrochloride | 0.001 | 0.5 |
| L-cystine dihydrochloride | 0.005 | 1.5 |
| L-glutamic acid | 0.01 | 1.5 |
| L-glutamic acid monosodium salt monohydrate | 0.01 | 1.5 |
| L-glutamine | 0.14 | 1.5 |
| L-glycine | 0.01 | 0.5 |
| L-histidine free base | 0.01 | 0.5 |
| L-histidine hydrochloride | 0.01 | 0.5 |
| hydroxy-L-proline | 0.01 | 0.25 |
| L-isoleucine | 0.1 | 0.75 |
| L-leucine | 0.01 | 0.75 |
| L-lysine | 0.01 | 1 |
| L-methionine | 0.05 | 0.5 |
| L-phenylalanine | 0.05 | 0.5 |
| L-proline | 0.1 | 1 |
| L-serine | 0.1 | 1 |
| L-threonine | 0.05 | 0.5 |
| L-tryptophan | 0.01 | 0.5 |
| L-tyrosinedisodium saltdihydrate | 0.01 | 0.5 |
| L-valine | 0.1 | 0.75 |
| L-ornithine | 0.001 | 0.05 |
| L-aspartic acid | 0.1 | 0.8 |
| L-alpha-aminobutyric acid | 0.001 | 0.025 |
| Gaba | 0.01 | 0.2 |
| l-carnosine | 0.01 | 1. |

16. A method for formulating an edible nutrient medium for the production of cultured meat for human consumption, comprising:
   (a) providing a plurality of ingredients including:
      (i) one or more of cyanocobalamin, an edible anti-foaming agent, and ferric ammonium citrate; and
      (ii) a plurality of amino acids within concentration ranges shown below:

| Amino Acids | Lowest Concentration (g/L) | Highest Concentration (g/L) |
| --- | --- | --- |
| L-alanine | 0.0001 | 0.5 |
| L-arginine | 0.01 | 2.5 |
| L-arginine hydrochloride | 0.01 | 1 |
| L-asparagine anhydrous | 0.1 | 1.5 |
| L-asparagine monohydrate | 0.01 | 0.9 |
| L-cysteine hydrochloride | 0.001 | 0.5 |
| L-cystine dihydrochloride | 0.005 | 1.5 |
| L-glutamic acid | 0.01 | 1.5 |
| L-glutamic acid monosodium salt monohydrate | 0.01 | 1.5 |
| L-glutamine | 0.14 | 1.5 |
| L-glycine | 0.01 | 0.5 |
| L-histidine free base | 0.01 | 0.5 |
| L-histidine hydrochloride | 0.01 | 0.5 |

-continued

| Amino Acids | Lowest Concentration (g/L) | Highest Concentration (g/L) |
|---|---|---|
| hydroxy-L-proline | 0.01 | 0.25 |
| L-isoleucine | 0.1 | 0.75 |
| L-leucine | 0.01 | 0.75 |
| L-lysine | 0.01 | 1 |
| L-methionine | 0.05 | 0.5 |
| L-phenylalanine | 0.05 | 0.5 |
| L-proline | 0.1 | 1 |
| L-serine | 0.1 | 1 |
| L-threonine | 0.05 | 0.5 |
| L-tryptophan | 0.01 | 0.5 |
| L-tyrosinedisodium saltdihydrate | 0.01 | 0.5 |
| L-valine | 0.1 | 0.75 |
| L-ornithine | 0.001 | 0.05 |
| L-aspartic acid | 0.1 | 0.8 |
| L-alpha-aminobutyric acid | 0.001 | 0.025 |
| Gaba | 0.01 | 0.2 |
| l-carnosine | 0.01 | 1 | and (b) mixing the plurality of ingredients in water to form the edible nutrient medium; wherein the nutrient medium does not comprise cobalt chloride, ammonium molybdate, ammonium metavanadate, sodium metavanadate, rubidium chloride, and strontium chloride hexahydrate.

17. The method of claim 16, wherein the nutrient medium does not comprise animal-derived components or animal-derived serums.

18. The method of claim 16, wherein the nutrient medium does not comprise: rubidium chloride, strontium chloride hexahydrate, hypoxanthine, putrescine, thymidine, and DL-alpha-lipoic acid.

19. The method of claim 16, wherein the plurality of ingredients includes methylcellulose.

* * * * *